US012569191B2

(12) United States Patent
Xu et al.

(10) Patent No.: US 12,569,191 B2
(45) Date of Patent: Mar. 10, 2026

(54) METHODS, DEVICES, AND SYSTEMS FOR PHYSIOLOGICAL PARAMETER ANALYSIS

(71) Applicant: ABBOTT DIABETES CARE INC., Alameda, CA (US)

(72) Inventors: Yongjin Xu, San Ramon, CA (US); Timothy C. Dunn, San Francisco, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 527 days.

(21) Appl. No.: 17/779,318

(22) PCT Filed: Nov. 24, 2020

(86) PCT No.: PCT/US2020/062056

§ 371 (c)(1),
(2) Date: May 24, 2022

(87) PCT Pub. No.: WO2021/108431

PCT Pub. Date: Jun. 3, 2021

(65) Prior Publication Data

US 2023/0027904 A1 Jan. 26, 2023

Related U.S. Application Data

(60) Provisional application No. 63/081,599, filed on Sep. 22, 2020, provisional application No. 63/015,044, (Continued)

(51) Int. Cl.
*A61B 5/00* (2006.01)
*A61B 5/145* (2006.01)
(Continued)

(52) U.S. Cl.
CPC ........ *A61B 5/4839* (2013.01); *A61B 5/14532* (2013.01); *A61B 5/746* (2013.01);
(Continued)

(58) Field of Classification Search
CPC ... A61B 5/4839; A61B 5/14532; A61B 5/746; A61M 5/1723; A61M 2230/201; G16H 10/40
See application file for complete search history.

(56) References Cited

U.S. PATENT DOCUMENTS 6,175,752 B1 1/2001 Say et al.
6,421,633 B1 7/2002 Heinonen et al.
(Continued)

FOREIGN PATENT DOCUMENTS

JP 10-332704 A 12/1998
JP 2003-528330 A 9/2003
(Continued)

OTHER PUBLICATIONS

Xu, Y. (2019). Correcting HBA1C Values for Individual Glycation Factors—Application of Red Blood Cell Glycation Kinetic Model Retrieved from https://dialog.proquest.com/professional/docview/2434986968?accountid= 131444 (Year: 2019).*
(Continued)

*Primary Examiner* — Jason M Sims
*Assistant Examiner* — Kyle W. Kretzer
(74) *Attorney, Agent, or Firm* — Workman Nydegger

(57) ABSTRACT

A method for deriving physiological parameters may include: measuring a glucose level of a subject over time; measuring a HbA1c of individual red blood cells in a sample comprising a plurality of red blood cells; deriving a measured cellular HbA1c distribution of the sample; and calculating at least one physiological parameter selected from the group consisting of (a) a red blood cell elimination constant ($k_{age}$), (b) a red blood cell glycation rate constant ($k_{gly}$), and/or (c) an apparent glycation constant (K) based on the measured cellular HbA1c distribution and the glucose levels of the subject over time.

20 Claims, 6 Drawing Sheets

Related U.S. Application Data filed on Apr. 24, 2020, provisional application No. 62/939,956, filed on Nov. 25, 2019.

(51) Int. Cl.
*A61M 5/172* (2006.01)
*G16H 10/40* (2018.01)

(52) U.S. Cl.
CPC .......... *A61M 5/1723* (2013.01); *G16H 10/40* (2018.01); *A61M 2230/201* (2013.01)

(56) References Cited

U.S. PATENT DOCUMENTS

| | | | |
|---|---|---|---|
| 2003/0212317 | A1 | 11/2003 | Kovatchev et al. |
| 2008/0009692 | A1 | 1/2008 | Stafford |
| 2011/0193704 | A1 | 8/2011 | Harper et al. |
| 2011/0213225 | A1 | 9/2011 | Bernstein et al. |
| 2011/0319729 | A1 | 12/2011 | Donnay et al. |
| 2014/0188400 | A1 | 7/2014 | Dunn et al. |
| 2014/0350369 | A1 | 11/2014 | Budiman et al. |
| 2015/0018639 | A1 | 1/2015 | Stafford |
| 2015/0025345 | A1 | 1/2015 | Funderburk et al. |
| 2015/0038816 | A1 | 2/2015 | Tokita et al. |
| 2015/0173661 | A1 | 6/2015 | Myles |
| 2018/0231573 | A1 | 8/2018 | Van Agthoven et al. |
| 2018/0235524 | A1* | 8/2018 | Dunn .................. A61M 5/1723 |
| 2018/0364262 | A1* | 12/2018 | Malka .................. G01N 33/723 |
| 2019/0142314 | A1 | 5/2019 | Masciotti et al. |
| 2021/0378561 | A1 | 12/2021 | Xu |
| 2023/0061350 | A1 | 3/2023 | Xu et al. |

FOREIGN PATENT DOCUMENTS

| | | | |
|---|---|---|---|
| JP | 2012-516735 | A | 7/2012 |
| JP | 2013-188240 | A | 9/2013 |
| JP | 2019-132839 | A | 8/2019 |
| WO | 2010/019372 | A1 | 2/2010 |
| WO | 2010/041439 | A1 | 4/2010 |
| WO | WO 2010/114929 | A1 | 10/2010 |
| WO | WO 2018/156584 | A1 | 8/2018 |
| WO | WO 2020/086934 | A2 | 4/2020 |

OTHER PUBLICATIONS

U.S. Appl. No. 62/750,957, filed Oct. 26, 2018, Xu.
U.S. Appl. No. 62/939,956, filed Nov. 25, 2019, Xu.
Bergenstal et al., "Glucose management indicator (GMI): A new term for estimating A1C from continuous glucose monitoring," Diabetes Care., 41(11): 2275-2280 (2018).
International Search Report mailed Feb. 23, 2021 corresponding to International Patent Application No. PCT/US2020/062056.
Malka et al., "Mechanistic modeling of hemoglobin glycation and red blood cell kinetics enables personalized diabetes monitoring," Sci Transl Med., 8(359), 359ra130 (2016).
Nathan et al., "Translating the A1C assay into estimated average glucose values," Diabetes Care 31(8): 1473-1478 (2008) PMID: 18540046.
Xu et al., "A Kinetic Model for Glucose Levels and Hemoglobin A1c Provides a Novel Tool for Individualized Diabetes Management,", J Diabetes Sci Technol., 15(2): 294-302 (2021) DOI: 10.1177/1932296819897613.
International Preliminary Report on Patentability received for PCT application No. PCT/US20/62040, mailed on Jun. 9, 2022, 11 pages.
International Preliminary Report on Patentability received for PCT application No. PCT/US20/62056, mailed on Jun. 9, 2022, 11 pages.
International search Report and written opinion received for PCT application No. PCT/US20/62040, mailed on Feb. 23, 2021, 13 pages.
Non-Final Office Action received for U.S. Appl. No. 17/779,370, mailed on Jun. 16, 2025, 16 pages.
Office Action received for Japanese Patent Application No. 2022-530750, mailed on Apr. 1, 2025, 4 pages (2 pages of English Translation and 2 pages of Original Document).
Requirement for Restriction/Election received for U.S. Appl. No. 17/779,370, mailed on Mar. 20, 2025, 6 pages.
Final Office Action received for U.S. Appl. No. 17/779,370, mailed on Nov. 14, 2025, 17 pages.
Office Action received for Canada Patent Application No. 3157577, mailed on Nov. 13, 2025, 5 pages.
Office Action received for Canada Patent Application No. 3157672, mailed on Nov. 14, 2025, 9 pages.
Office Action received for Chinese Patent Application No. 202080094338.1, mailed on Jan. 12, 2026, 10 pages.
Office Action received for Japanese Patent Application No. 2022-530750, mailed on Jan. 20, 2026, 5 pages (3 pages of English Translation and 2 pages of Original Document).

* cited by examiner

210

216 → 212 →218

214

310

SERVER/CLOUD
328

DATA NETWORK
322

HEALTH MONITORING
DEVICE                                              320

GLUCOSE
MONITOR                    324

SUBJECT INTERFACE
320A

ANALYSIS MODULE
320B

326          DATA
PROCESSING
TERMINAL/PC

METHODS, DEVICES, AND SYSTEMS FOR PHYSIOLOGICAL PARAMETER ANALYSIS

CROSS-REFERENCE TO RELATED APPLICATIONS

The present application is a U.S. National Stage Patent Application under 35 U.S.C. § 371 of International Patent Application No. PCT/US2020/062056-filed Nov. 24, 2020, which claims priority to US Provisional Patent Application No. 62/939,956 filed Nov. 25, 2019, U.S. Provisional Patent Application No. 63/015,044 filed Apr. 24, 2020, and U.S. Provisional Patent Application No. 63/081,599 filed Sep. 22, 2020, the contents of each of which are hereby incorporated herein in their entireties.

STATEMENT REGARDING FEDERALLY SPONSORED RESEARCH OR DEVELOPMENT

Not applicable.

BACKGROUND

The measurement of various analytes within an individual can sometimes be vital for monitoring the condition of their health. During normal circulation of red blood cells in a mammal such as a human body, glucose molecules attach to hemoglobin, which is referred to as glycosylated hemoglobin (also referred to as glycated hemoglobin). The higher the amount of glucose in the blood, the higher the percentage of circulating hemoglobin molecules with glucose molecules attached. The level of glycosylated hemoglobin is increased in the red blood cells of subjects with poorly controlled diabetes mellitus. Since glucose molecules stay attached to hemoglobin for the life of the red blood cells (normally no more than about 120 days), the level of glycosylated hemoglobin reflects an average blood glucose level over that period.

Most of hemoglobin is a type called HbA. When glucose molecules attach to HbA molecules, glycosylated HbA is formed, which is referred to as HbA1. HbA1 has three components: HbA1a, HbA1b, and HbA1c. Because a glucose binds more strongly and to a higher degree to HbA1c than HbA1a and HbA1b, a measure of HbA1c in blood (HbA1c test) is often used as an indication of a subject's average blood glucose level over a 100-120 day period (the average lifetime of a red blood cell). The HbA1c test is performed by drawing a blood sample from a subject at a medical professional's office, which is then analyzed in a laboratory. The HbA1c test may be used as a screening and diagnostic test for pre-diabetes and diabetes. The HbA1c test may be conducted multiple times over a time period to monitor the health of a subject for diagnosis and/or therapy decisions.

Commercially available in vitro blood glucose test strips and in vivo sensors (and their related devices and systems) provide glucose level measurements with varying degree of measurement frequency. These devices also provide an estimated HbA1c ("eHbA1c") value. While both in vitro and in vivo sensors (and their related devices and systems) are known to be reliable and accurate, when comparisons have been made between HbA1c values and eHbA1c values, a notable discrepancy between the two measurements has been observed. Existing eHbA1c methods and devices, with their reliance on static models, and/or broad assumptions and/or less robust data, are generally considered to be less reliable than HbA1c test results. However, HbA1c determination is inconvenient and uncomfortable for subjects, who must periodically have blood drawn for HbA1c tests and then wait for the results. Additionally, subjects and healthcare providers would benefit from a more accurate eHbA1c that would allow both subjects and their health care providers to monitor and respond to any changes in eHbA1c. Thus, a need exists for improved eHbA1c methods and devices.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
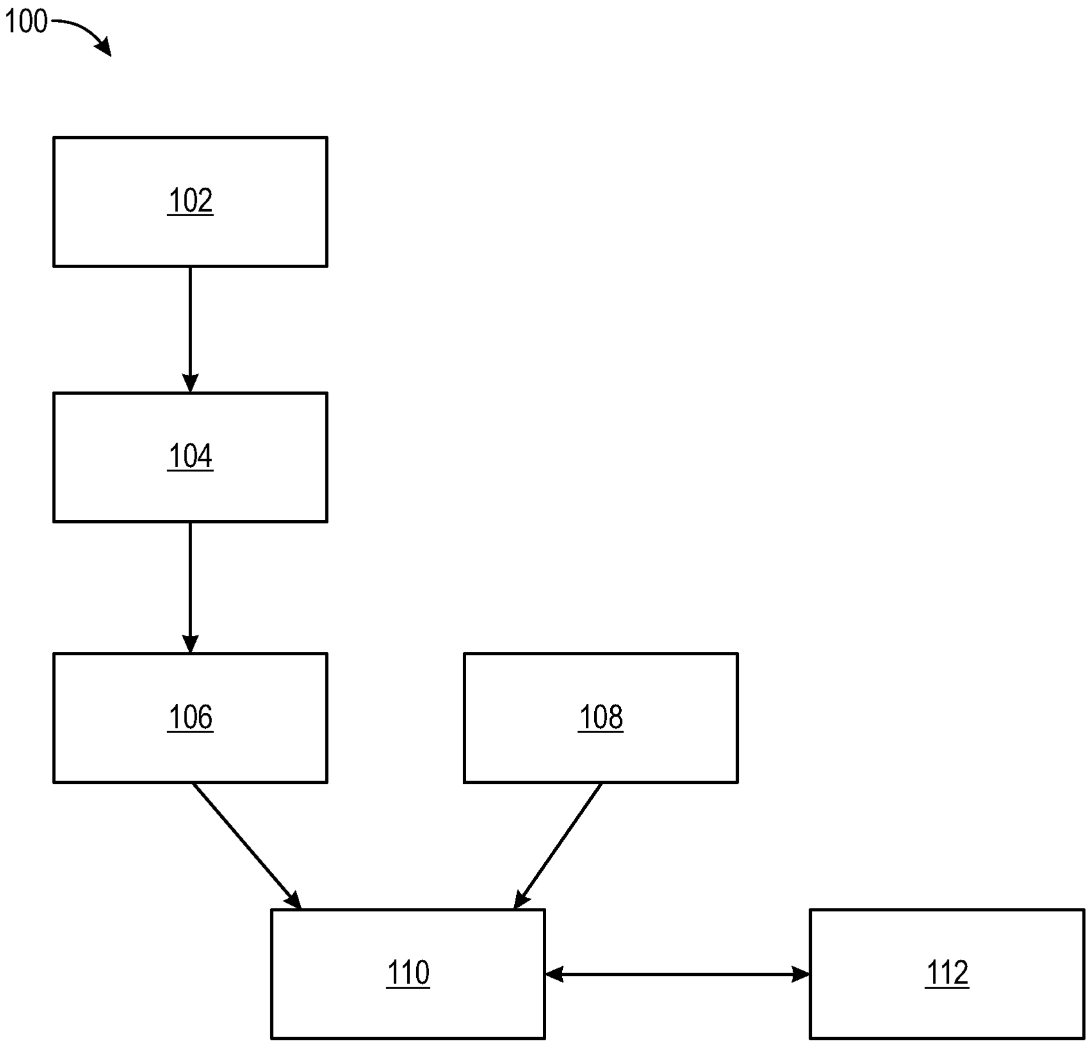
FIG. 1 illustrates a flow of a nonlimiting example of a method 100 of the present disclosure.

The present disclosure generally describes methods, devices, and systems for determining physiological parameters related to the kinetics of red blood cell hemoglobin glycation, elimination, and generation within the body of a subject. Such physiological parameters can be used, for example, to calculate a more reliable calculated HbA1c and/or a personalized target glucose range, among other things.

Herein, the terms "HbA1c level," "HbA1c value," and "HbA1c" are used interchangeably. Herein, the terms "aHbA1c level," "aHbA1c value," and "aHbA1c" are used interchangeably. Herein, the terms "cHbA1c level," "cHbA1c value," and "cHbA1c" are used interchangeably.

Kinetic Model

Formula 1 illustrates the kinetics of red blood cell hemoglobin glycation (or referred to herein simply as red blood cell glycation), red blood cell elimination, and red blood cell generation, where "G" is free glucose, "R" is a non-glycated red blood cell, and "GR" is s glycated red blood cell hemoglobin. The rate at which glycated red blood cell hemoglobin (GR) are formed is referred to herein as a red blood cell hemoglobin glycation rate constant ($k_{gly}$ typically having units of dL*mg$^{-1}$*day$^{-1}$ and also referred to herein as red blood cell glycation rate constant).

Formula 1

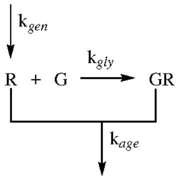

Over time, red blood cell hemoglobin including the glycated red blood cell hemoglobin are continuously eliminated from a subject's circulatory system and new red blood cells containing hemoglobin are generated, typically at a rate of approximately 2 million cells per second. The rates associated with elimination and generation are referred to herein as a red blood cell elimination constant ($k_{age}$ typically having units of day$^{-1}$) and a red blood cell generation rate constant ($k_{gen}$ typically having units of $M^2$/day), respectively. Since the amount of red blood cells in the body is maintained at a stable level most of time, the ratio of $k_{age}$ and $k_{gen}$ should be an individual constant that is the square of red blood cell concentration.

Relative to glycation, Formula 2 illustrates the mechanism in more detail where glucose transporter 1 (GLUT1) facilitates glucose (G) transport into the red blood cell. Then, the intracellular glucose (GI) interacts with the hemoglobin (Hb) to produce glycated hemoglobin (HbG) where the hemoglobin glycation reaction rate constant is represented by $k_g$ (typically having units of dL*mg$^{-1}$*day$^{-1}$). $k_g$ is related to $k_{gly}$ per Equation 1 where $k_g$ is a component of $k_{gly}$.

Formula 2

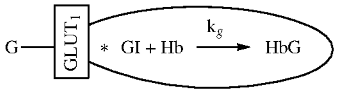

$$k_{gly} = k_g * V_{max}/(k_c * k_M) \quad \text{Equation 1}$$

where $k_c$ is the rate constant for glucose consumption in the red blood cell (typically having units of day$^{-1}$); $V_{max}$ is the maximum glucose transport rate (typically having units of mg*dL$^{-1}$*day$^{-1}$) and should be proportional to the GLUT1 level on the membrane; and $K_M$ is the Michaelis-Menten kinetic rate constant for the GLUT1 transporting glucose across the red blood cell membrane (typically having units of mM or mg/dL). The $k_{gly}$, in Equation 1, has the units of dL*mg$^{-1}$*day$^{-1}$.

$k_g$ and $K_M$ are values that vary between individuals by very little, if at all, and is, therefore, assumed to be constant values herein. A typical experiment measured $k_g$ value is $1.2\times10^{-3}$ dL/mg/day. Hemoglobin glycation reaction is a multi-step non-enzymatic chemical reaction, therefore $k_g$ should be a universal constant. $K_M$ is the Michaelis constant that relates to the affinity of an enzyme (e.g., GLUT1) for a substrate (e.g., glucose). $K_M$ is determined experimentally. Different values for the $K_M$ for RBC GLUT1-glucose interaction have been reported in the literature ranging from about 100 mg/dL to about 700 mg/L. Two specific example values are 306 mg/dL and 472 mg/dL.

As described previously, HbA1c is a commonly used analyte indicative of the fraction of the glycated hemoglobin found in red blood cells. Therefore, a kinetic model can be used, for example, to derive a calculated HbA1c based on at least the glucose levels measured for a subject. However, the kinetic model can also be applied to HbA1. For simplicity, HbA1c is uniformly used herein, but HbA1 could be substituted except in instances where specific HbA1c values are used. In such instances, specific HbA1 values could be used to derive similar equations.

Typically, when kinetically modeling physiological processes, assumptions are made to focus on the factors that affect the physiological process the most and simplify some of the math.

The present disclosure uses only the following set of assumptions to kinetically model the physiological process illustrated in Formulas 1 and 2. First, there is an absence of any abnormal red blood cells that would affect HbA1c measurements. Second, the glycation process has first-order dependencies on concentrations of both hemoglobin in red blood cells and intracellular glucose, an assumption that is widely adopted. Third, newly-generated red blood cells have a negligible amount of glycated hemoglobin. Finally, red blood cells are eliminated from circulation when they reach a subject specific age. The individual red blood cell elimination rate is approximated with a constant. Therefore, the glycated hemoglobin removal rate is proportional to the product of overall red blood cell elimination rate and HbA1c at the time.

With these assumptions described above for this kinetic model of single red blood cell under glucose exposure, slow conversion of non-glycated hemoglobin (R) to glycated hemoglobin (GR) in red blood cell should happen under per Equation 2.

$$\frac{d[GR]}{dt} = k_g[GI][R] \quad \text{Equation 2}$$

where C=[R]+[GR] (Equation 3), or the whole population of hemoglobin in red blood cells where C typically has units of M (molar), where [R] and [GR] typically have units of M (molar), and where [G] typically has units of mg/dL.

Assuming (a) a steady state where the glucose level is constant and the glycated and non-glycated red blood cell concentrations remain stable (d[GR]/dt=(d[R])/dt=0) and (b) H(0) is 0% because the cell has not been exposed to glucose, then Equations 4 and 5 can be derived. Further, Equation 5 can be further generalized to Equation 6 because $k_{gly}$ and [G] are considered constant at steady state.

$$H(t)=1+(H(0)-1)*e^{-k_g[GI]t} \quad \text{Equation 4}$$

where H is the single red blood cell HbA1c value having units of %, t is the age of the red blood cell having units of days, and [GI] is the concentration of intracellular glucose having the units of mg/dL $$k_g[GI]t=-\ln(1-H(t)) \quad \text{Equation 5}$$

$$t\propto-\ln(1-H(t)) \quad \text{Equation 6}$$

Therefore, the age of a red blood cell (t) is proportional to the HbA1c value of said red blood cell. The relationship between cell age and HbA1c value is provided in Equation 4. Under variable glucose for a single red blood cell, Equation 4 becomes Equation 7.

$$H(t)=1-e^{-k_g\int_0^t GI(t)dt}=1-e^{-k_g*AGI(t)*t} \qquad \text{Equation 7}$$

where AGI(t) is the cumulative average intracellular glucose up to time t

Therefore, Equation 8 is HbA1c value of a red blood cell i days old, and Equation 9 is the concentration of intracellular glucose ([GI]).

$$H(i)=1-e^{-k_g*AGI(i)*i} \qquad \text{Equation 8}$$

where $$AGI(i)=\frac{\sum_{i=0}^{i} GI(i)}{i+1}$$

$$[GI]=g*k_{gly}/k_g \qquad \text{Equation 9}$$

where $g=(K_M*[G])/(K_M+[G])$

Further, the age distribution for red blood cells p(d) follows Equation 10 where an assumption that the distribution is a mixture of fixed live and random elimination.

$$p(d)=\frac{k_{age}\left[(1+T)e^{-k_{age}d}-T\right]}{1-T*\ln\left(\frac{1+T}{T}\right)},\ \text{when } d<A_{max} \qquad \text{Equation 10}$$

$$p(d)=0,\ \text{when } d\geq A_{max}$$

where $$A_{max}=\frac{\ln\left(\frac{1+T}{T}\right)}{k_{age}};$$

T is an individualized unitless constant and should be greater than 0 and less than 1; and d is the age in days The fraction of red blood cells i days old (F(i)) is derived from Equation 10 to get Equation 11.

$$F(i)=B[(1+T)e^{-*k_{age}}-T] \qquad \text{Equation 11}$$

where $$B=\frac{k_{age}}{1-T*\ln\left(\frac{1+T}{T}\right)}$$

Alternative to Equations 10 and 11, if a fixed life-span is assumed for red blood cells, Equation 12 may be used in the methods and systems described herein.

$$F(i)=\frac{1}{k_{age}}\ \text{when } i\leq 1/k_{age} \qquad \text{Equation 12}$$

$$F(i)=0\ \text{when } i>1/k_{age}$$

The methods of the present disclosure exploit the foregoing relationships to derive rate constants $k_{age}$ and $k_{gly}$ and, consequently K (apparent glycation constant equal to $k_{gly}/k_{age}$) and $k_{gen}$.

FIG. 1 illustrates a flow of a nonlimiting example of a method 100 of the present disclosure. The glucose level of a subject (also referred to herein as a patient) is measured over time (e.g., 1 month or more) to provide [G] as a function of t ([G](t) 102). [G](t) 102 can be converted to [GI] as a function of t ([GI](t) 104) using $k_{gly}$. [GI](t) 104 can be converted to HbA1c value as a function of cell age (H(i) 106, Equation 8). Separately, the age distribution (F(i) 108, Equation 11 and/or Equation 12) of red blood cells is related to $k_{age}$. Using H(i) 106 derived from glucose level measurements and the F(i) 108 based on an estimated $k_{age}$, a derived individual cell HbA1c distribution 110 (e.g., mathematical representation like a plot, an equation, a table, and the like) of the number of individual red blood cells having specific HbA1c values is derived. More specifically, the individual red blood cells in the F(i) 108 are assigned a HbA1c value per the H(i) 106.

Further, the HbA1c values for individual red blood cells in a patient sample are measured to give a measured individual cell HbA1c distribution 112, which is compared to the derived individual cell HbA1c distribution 110. Then, $k_{age}$ and $k_g$ (or $k_{gly}$) are iteratively adjusted to improve the fit of the derived individual cell HbA1c distribution 110 to the measured individual cell HbA1c distribution 112.

The kinetic constants $k_{age}$, $k_{gly}$, and K (apparent glycation constant equal to $k_{gly}/k_{age}$) for each individual can then be applied in a variety of applications including, but not limited to:

(a) a calculated HbA1c;
(b) a corrected HbA1c;
(c) a personalized-target glucose range;
(d) a personalized-target average glucose;
(e) a personalized treatment for subject triage;
(f) a personalized treatment for titration of diabetes medication;
(g) a personalized closed-loop or hybrid-closed loop control system;
(h) a personalized treatment using glycation medications;
(i) identification of abnormal or diseased physiological conditions;
(j) identification of supplements and/or medicines present during testing; and
(k) determination of physiological age.

Further, one or more of (a)-(k) may be used as a basis for administering and/or adjusting treatment of a patient. Such treatments may include, but are not limited to, an insulin dosage, a glycation medication dosage, an exercise regime, a meal intake, or a combination thereof. Administering and/or adjusting of such treatments generally would be based on current treatment methods but using the personalized values of (a)-(k) rather than said values currently used as the basis for such treatment.

Individual Cell HbA1c Measurements

In one example, the HbA1c value for individual red blood cells can be determined using spectroscopic techniques like fluorescence, refractometry, and Raman spectroscopy as described in Lazareva et al. Proc. SPIE 10685, Biophotonics: Photonic Solutions for Better Health Care VI, 1068540 (17 May 2018). Of the foregoing, fluorescence is preferred because flow cytometry may be used to quickly and accurately measure the fluorescent emission of individual blood cells. More specifically relative to fluorescence, hemoglobin excited at 160 nm or 270 nm has a different emission wavelength depending on the hemoglobin is glycated (HbA1c) or non-glycated (Hb). Therefore, the level of HbA1c in an individual blood cell is proportional to the intensity of the emission fluorescence. Flow cytometry can measure the fluorescent emission of individual blood cells. Accordingly, flow cytometry of red blood cells with an excitation wavelength of 160 nm or 270 nm yields a measure of the HbA1c value for a plurality of cells on an individual bases or a distribution of individual cell HbA1c values in a blood sample.

In another example, the HbA1c value for individual red blood cells can be determined using fluorescently tagged antibodies specific to HbA1c (fluorescent anti-HbA1c). Briefly, blood cells are stabilized, permeated, stained with fluorescent anti-HbA1c and a fluorescent RNA marker (wherein the fluorescent anti-HbA1c and the fluorescent RNA marker emit at different wavelengths), and analyzed by flow cytometry as described in US Patent App. No. 2018/0231573, which is incorporated herein by reference.

While flow cytometry is described herein as preferable because of high throughput, fast sample analysis time, and accuracy, other methods of measuring the HbA1c value for individual red blood cells may be used in the methods and systems described herein.

Measuring Glucose Levels

The measurement of the plurality of glucose levels described herein may be done with in vivo and/or in vitro (ex vivo) methods, devices, or systems for measuring at least one analyte, such as glucose, in a bodily fluid such as in blood, interstitial fluid (ISF), subcutaneous fluid, dermal fluid, sweat, tears, saliva, or other biological fluid. In some instances, in vivo and in vitro methods, devices, or systems may be used in combination.

Examples of in vivo methods, devices, or systems measure glucose levels and optionally other analytes in blood or ISF where at least a portion of a sensor and/or sensor control device is, or can be, positioned in a subject's body (e.g., below a skin surface of a subject). Examples of devices include, but are not limited to, continuous analyte monitoring devices and flash analyte monitoring devices. Specific devices or systems are described further herein and can be found in U.S. Pat. No. 6,175,752 and US Patent Application Publication No. 2011/0213225, the entire disclosures of each of which are incorporated herein by reference for all purposes.

In vitro methods, devices, or systems (including those that are entirely non-invasive) include sensors that contact the bodily fluid outside the body for measuring glucose levels. For example, an in vitro system may use a meter device that has a port for receiving an analyte test strip carrying bodily fluid of the subject, which can be analyzed to determine the subject's glucose level in the bodily fluid. Additional devices and systems are described further below.

The frequency and duration of measuring the glucose levels may vary from, on average, about 3 times daily (e.g., about every 8 hours) to about 14,400 times daily (e.g., about every 10 seconds) (or more often) and from about a few days to over about 300 days, respectively.

Once glucose levels are measured, the glucose levels may be used to in combination with the measured individual cell HbA1c distribution determine the one or more physiological parameters ($k_{gly}$, $k_{age}$, and/or K) and, optionally, other analyses (e.g., cHbA1c, aHbA1c, personalized target glucose range, and others described herein). In some instance, such analyses may be performed with a physiological parameter analysis system. For example, in some embodiments, the glucose monitor may comprise a glucose sensor coupled to electronics for (1) processing signals from the glucose sensor and (2) communicating the processed glucose signals to one or more of health monitoring device, server/cloud, and data processing terminal/PC.

Once glucose levels are measured, the glucose levels may be used to determine the one or more physiological parameters and, optionally, other analyses described herein. In some instance, such analyses may be performed with a physiological parameter analysis system. For example, in some embodiments, an individual cell HbA1c distribution may be measured with a laboratory test where the results are input to the server/cloud, the subject interface, and/or a display from the testing entity, a medical professional, the subject, or other user. Then, the individual cell HbA1c distribution may be received by the one or more of health monitoring device, server/cloud, and data processing terminal/PC for analysis by one or more methods described herein.

Systems

In some embodiments, the one or more physiological parameters ($k_{gly}$, $k_{age}$, and/or K) determined by the methods described herein may be applied to systems.

Figure 2:
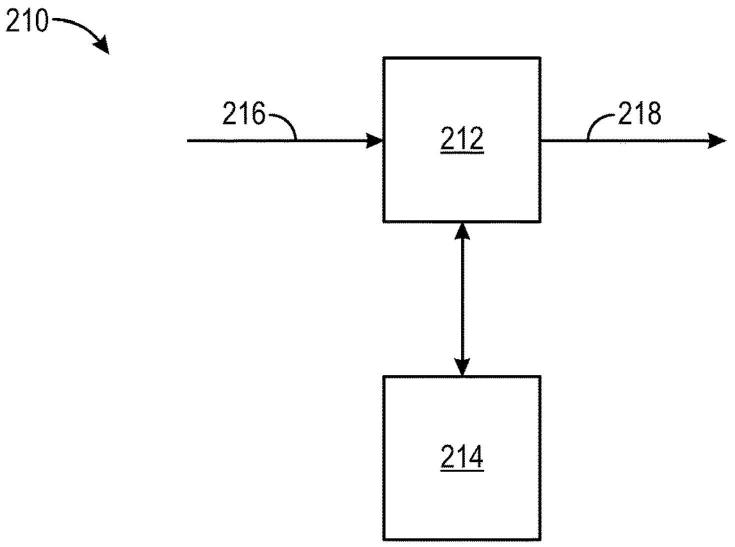
FIG. 2 illustrates an example of a system for applying physiological parameters determined by methods described herein in accordance with some of the embodiments of the present disclosure.

FIG. 2 illustrates an example of a system 210 for using the one or more physiological parameters in accordance with some of the embodiments of the present disclosure. The system 210 includes one or more processors 212 and one or more machine-readable storage media 214. The one or more machine-readable storage media 214 contains a set of instructions for performing an analysis routine, which are executed by the one or more processors 212.

In some embodiments, the instructions include receiving inputs 216 (e.g., one or more physiological parameters ($k_{gly}$, $k_{age}$, and/or K) determined as described herein and, optionally, one or more glucose levels, one or more HbA1c values, or more other subject-specific parameters, and/or one or more times associated with any of the foregoing), determining outputs 218 (e.g., an error associated with the one or more physiological parameters, one or more parameters or characteristics for a subject's personalized diabetes management (e.g., cHbA1c, aHbA1c, a personalized-target glucose range, an average-target glucose level, a supplement or medication dosage, among other parameters or characteristics), and the like), and communicating the outputs 218. In some embodiments, communication of the inputs 216 may be via a user-interface (which may be part of a display), a data network, a server/cloud, another device, a computer, or any combination thereof, for example. In some embodiments, communication of the outputs 218 may be to a display (which may be part of a user-interface), a data network, a server/cloud, another device, a computer, or any combination thereof, for example.

A "machine-readable medium", as the term is used herein, includes any mechanism that can store information in a form accessible by a machine (a machine may be, for example, a computer, network device, cellular phone, personal digital assistant (PDA), manufacturing tool, any device with one or more processors, and the like). For example, a machine-accessible medium includes recordable/non-recordable media (e.g., read-only memory (ROM), random access memory (RAM), magnetic disk storage media, optical storage media, flash memory devices, and the like).

In some instances, the one or more processors 212 and the one or more machine-readable storage media 214 may be in a single device (e.g., a computer, network device, cellular phone, PDA, an analyte monitor, and the like).

Figure 3:
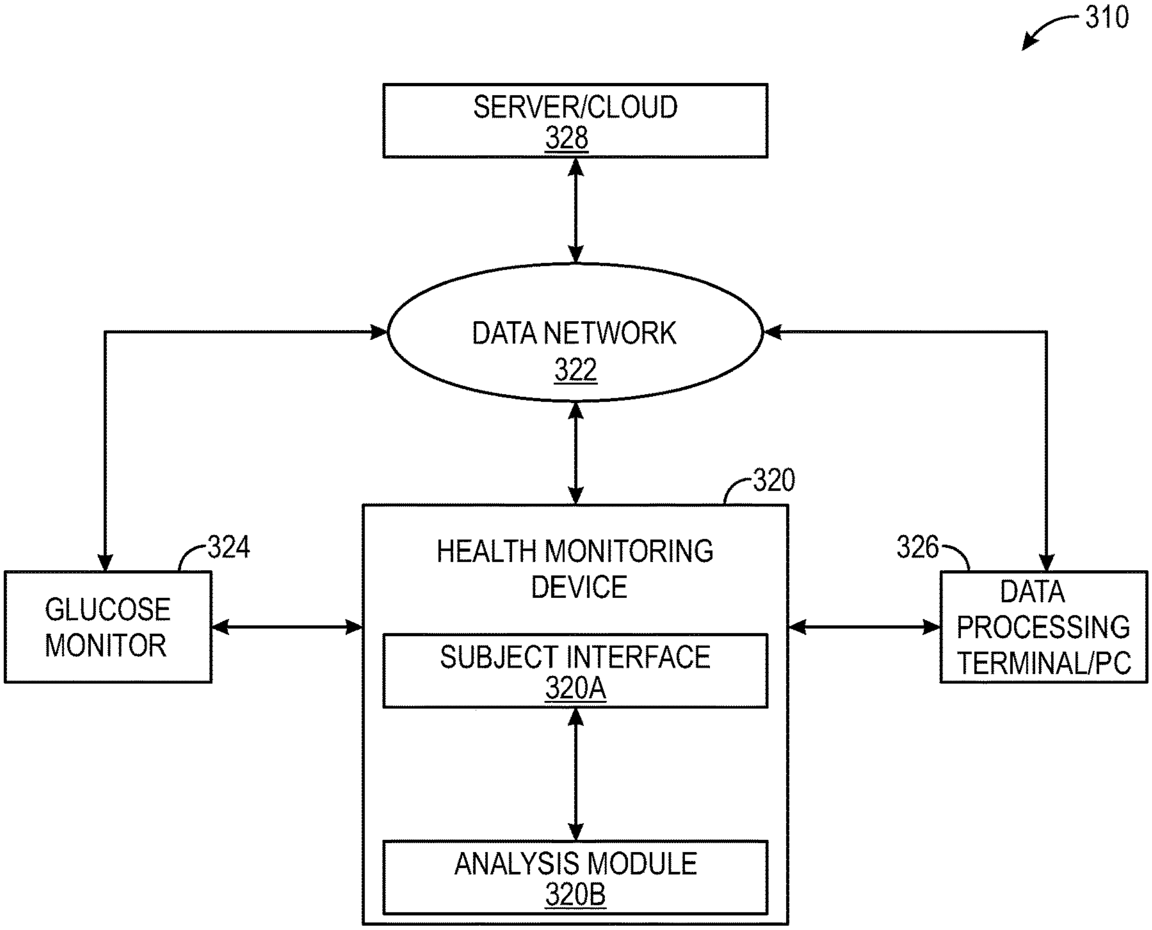
FIG. 3 illustrates an example of a system for applying physiological parameters determined by methods described herein in accordance with some of the embodiments of the present disclosure.

In some embodiments, such a system may include other components. FIG. 3 illustrates another example of a system 310 for applying the physiological parameters described herein in accordance with some of the embodiments of the present disclosure.

The system 310 includes health monitoring device 320 with subject interface 320A and analysis module 320B, the health monitoring device 320 is, or may be, operatively coupled to data network 322. Also provided in system 310 is a glucose monitor 324 (e.g., in vivo and/or in vitro (ex vivo) devices or system) and a data processing terminal/personal computer (PC) 326, each operatively coupled to health monitoring device 320 and/or data network 322. Further shown in FIG. 3 is server/cloud 328 operatively coupled to data network 322 for bi-directional data communication with one or more of health monitoring device 320, data processing terminal/PC 326 and glucose monitor 324. System 310 within the scope of the present disclosure can exclude one or more of server/cloud 328, data processing terminal/PC 326 and/or data network 322.

In certain embodiments, analysis module 320B is programmed or configured to perform analyses based, at least in part on, the one or more physiological parameters ($k_{gly}$, $k_{age}$, and/or K) determined as described herein (e.g., to determine a value for or if a value is outside specific limits for: cHbA1c, aHbA1c, personalized target glucose range, and others described herein). As illustrated, analysis module 320B is a portion of the health monitoring device 320 (e.g., executed by a processor therein). However, the analysis module 320B may alternatively be associated with one or more of server/cloud 328, glucose monitor 324, and/or data processing terminal/PC 326. For example, one or more of server/cloud 328, glucose monitor 324, and/or data processing terminal/PC 326 may comprise machine-readable storage medium (media) with a set of instructions that cause one or more processors to execute the set of instructions corresponding to the analysis module 320B.

While the health monitoring device 320, the data processing terminal/PC 326, and the glucose monitor 324 are illustrated as each operatively coupled to the data network 322 for communication to/from the server/cloud 328, one or more of the health monitoring device 320, the data processing terminal/PC 326, and the glucose monitor 324 can be programmed or configured to directly communicate with the server/cloud 328, bypassing the data network 322. The mode of communication between the health monitoring device 320, the data processing terminal/PC 326, and the glucose monitor 324 and the data network 322 includes one or more wireless communication, wired communication, RF communication, BLUETOOTH® communication, WiFi data communication, radio frequency identification (RFID) enabled communication, ZIGBEE® communication, or any other suitable data communication protocol, and that optionally supports data encryption/decryption, data compression, data decompression and the like.

The analyses can be performed by one or more of the health monitoring device 320, data processing terminal/PC 326, glucose monitor 324, and server/cloud 328, with the resulting analysis output shared in the system 310.

Additionally, while the glucose monitor 324, the health monitoring device 320, and the data processing terminal/PC 326 are illustrated as each operatively coupled to each other via communication links, they can be modules within one integrated device (e.g., sensor with a processor and communication interface for transmitting/receiving and processing data).

Calculated HbA1c (cHbA1c)

After one or more physiological parameters ($k_{gly}$, $k_{age}$, and/or K) are calculated, a plurality of glucose measurements may be taken for a following time period and used for calculating HbA1c during and/or at the end of the following time period.

Assuming a steady state, where the glucose level is constant and the glycated and non-glycated red blood cell concentrations remain stable (d[GR]/dt=(d[R])/dt=0), the following two equations can be derived. Equation 13 defines the apparent glycation constant K (typically with units of dL/mg) as the ratio of $k_{gly}$ and $k_{age}$, whereas Equation 14 establishes the dependency between red blood cell generation and elimination rates.

$$K=k_{gly}/k_{age}=[GR]/g[R] \quad \text{Equation 13}$$

$$k_{gen}/k_{age}=C^2 \quad \text{Equation 14}$$

where $g=(K_M*[G])/(K_M+[G])$

For simplicity, $k_{age}$ is used hereafter to describe the methods, devices, and systems of the present disclosure. Unless otherwise specified, $k_{gen}$ can be substituted for $k_{age}$. To substitute $k_{gen}$ for $k_{age}$, Equation 14 would be rearranged to $k_{gen}=k_{age}*C^2$.

HbA1c is the fraction of glycated hemoglobin as shown in Equation 15.

$$HbA1c=[GR]/C=(C-[R])/C \quad \text{Equation 15}$$

In a hypothetical state when a person infinitely holds the same glucose level, HbA1c in Equation 15 can be defined as "equilibrium HbA1c" (EA) (typically reported as a % (e.g., 6.5%) but used in decimal form (e.g., 0.065) in the calculations). For a given glucose level, EA (Equation 16) can be derived from Equations 3, 13, and 15.

$$EA=g/(K^{-1}+g) \quad \text{Equation 16}$$

EA is an estimate of HbA1c based on a constant glucose concentration [G] for a long period. This relationship effectively approximates the average glucose and HbA1c for an individual having a stable day-to-day glucose profile.

Therefore, glucose levels over time can be averaged to give [AG]. The $k_{age}$ and $k_{gly}$ (or K) calculated above and [AG] can be used per Equation 17 to give a calculated HbA1c (cHbA1c) in a steady state.

$$\text{cHbA1}c=(k_{gly}[AG])/(k_{age}+k_{gly}[AG])=[AG]/(K^{-1}+[AG]) \quad \text{Equation 17}$$

Over time a patient's day-to-day average glucose level may change. As such, cHbA1c can be calculated with Equation 18.

$$cHbA1c = EA_z(1-D_z) + \sum_{i=1}^{z-1}\left[EA_i(1-D_i)\prod_{i=i+1}^{z} D_j\right] + HbA1c_0\prod_{j=1}^{z} D_j \quad \text{Equation 18}$$

where $D_i=e^{-(k_{gly}*g_i+k_{age})t_i}$, $EA_i=g_i/(K^{-1}+g_i)$, and $g_i=(K_M*[G_i])/(K_M+[G_i])$.

In Equation 18, the $HbA1c_0$ is a previously measured lab HbA1c value. When the time since the last HbA1c test were partitioned into even intervals, usually no longer than 1 day each, the $G_i$ and $t_i$ are average glucose and length of the time in a given interval.

Greater frequency of glucose monitoring and a longer period of time over which the glucose is monitored may provide a more accurate cHbA1c.

In some instances, a cHbA1c may be compared to a previous cHbA1c and/or a previous measured HbA1c (or corrected HbA1c described further herein) to monitor the efficacy of a subject's personalized diabetes management. For example, if a diet and/or exercise plan is being implemented as part of a subject's personalized diabetes management, with all other factors (e.g., medication and other diseases) equal, then changes in the cHbA1c compared to the previous cHbA1c and/or the previous measured HbA1c value may indicate if the diet and/or exercise plan is effective, ineffective, or a gradation therebetween.

In some instances, a cHbA1c may be compared to a previous cHbA1c and/or a previous measured HbA1c (or corrected HbA1c described further herein) to determine if $k_{age}$ and $k_{gly}$ should be derived per the methods described herein and/or a HbA1c measurement should be taken. For example, in absence of significant glucose profile change, the cHbA1c changes by 0.5 percentage units or more (e.g., changes from 7.0% to 6.5% or from 7.5% to 6.8%) as compared to the previous cHbA1c and/or the previous measured HbA1c value (or corrected HbA1c described further herein) may trigger deriving new $k_{age}$ and $k_{gly}$ values per the methods described herein and/or taking a HbA1c measurement.

In some instances, a comparison of the cHbA1c to a previous cHbA1c and/or a previous measured HbA1c value (or corrected HbA1c described further herein) may indicate if an abnormal or diseased physiological condition is present. For example, if a subject has maintained a cHbA1c and/or measured HbA1c value (or corrected HbA1c described further herein) for an extended period of time, then if a change in cHbA1c is identified with no other obvious causes, the subject may have a new abnormal or diseased physiological condition. Indications of what that new abnormal or diseased physiological condition may be gleaned from the one or more physiological parameters ($k_{gly}$, $k_{age}$, and/or K). Details of abnormal or diseased physiological conditions relative to the one or more physiological parameters are discussed further herein.

Adjusted HbA1c

In the diabetes and red blood cell hemoglobin glycation arts, the generally accepted average RBC lifespan may change. While the reference RBC lifespan may be outside these ranges, the $k^{ref}_{age}$ preferably reflects a reference average RBC lifespan of 85 days to 135 days, or 85 days to 110 days, or 90 days to 110 days, or 95 days to 125 days, or 110 days to 135 days. Most preferably, the $k^{ref}_{age}$ reflects a reference RBC lifespan of 85 days to 110 days, or 90 days to 110 days, or 100 days. Herein, $k^{ref}_{age}$ equals 0.01 $day^{-1}$ for all examples. However, embodiments of the present disclosure are not limited to this specific $k^{ref}_{age}$.

The aHbA1c for a subject can be calculated via Equation 19 using the HbA1c level for said subject, the $k_{age}$ for said subject, and the $k^{ref}_{age}$.

$$aHbA1c = \frac{HbA1c}{HbA1c + \frac{k^{ref}_{age}}{k_{age}}(1 - HbA1c)} \quad \text{Equation 19}$$

where HbA1c may be cHbA1c described herein or a laboratory measured HbA1c

Usually, $K=k_{gly}/k_{age}$ requires only one data section to determine in high confidence. Since a larger K value usually correlates with smaller $k_{age}$ values, it is possible to generate an approximate aHbA1c with K in the early stage of data acquisition when $k_{age}$ is not yet available (Equation 20). A typical $K^{ref}$ value is, for example, $5.2\times10^{-4}$ dL/mg. However, embodiments of the present disclosure are not limited to this specific $K^{ref}$.

$$aHbA1c = \frac{HbA1c}{HbA1c + \frac{K}{K^{ref}}(1 - HbA1c)} \quad \text{Equation 20}$$

where HbA1c may be cHbA1c described herein or a laboratory measured HbA1c

The aHbA1c for a subject (based, at least in part, on a measured HbA1c and/or a calculated HbA1c) can then be used for diagnoses, treatments, and/or monitoring protocols of said subject. For example, the subject may be diagnosed with diabetes, pre-diabetes, or another abnormal or diseased physiological condition based, at least in part, on the aHbA1c described herein. In another example, the subject may be monitored and/or treated with insulin self-monitoring and/or injections, continuous insulin monitoring and/or injections, and the like based, at least in part, on the aHbA1c described herein. In yet another example, the aHbA1c described herein may be used for determining and/or administering a personalized treatment for subject triage, determining and/or administering a personalized treatment for titration of diabetes medication, determining and/or administering a personalized closed-loop or hybrid-closed loop control system, determining and/or administering a personalized treatment using glycation medications, determining of physiological age, identifying if and/or what supplements and/or medicines are present during testing, and the like, and any combination thereof.

By removing the interference from RBC turnover rate variation, aHbA1c is a better individual biomarker than HbA1c for the risk of complications in people with diabetes. The aHbA1c can be higher and lower than measured HbA1c and which will make significant differences in diabetes diagnosis and management. For an individual with faster than usual RBC turnover rate, a typical observation in patients with kidney disease or after heart valve surgery, HbA1c is artificially low and give people illusion of good glycemic control. In contrary, slower than normal RBC turnover will lead to artificially high HbA1c and lead to over-zealous treatment and may cause dangerous hypoglycemia.

In an example, a $k_{age}$ of 0.0125 $day^{-1}$ (or RBC lifespan of 80 days) and measured HbA1c 7% would lead to aHbA1c of 8.6%. A measured HbA1c of 7% without adjustment for RBC turnover rate indicates good glycemic control. However, said HbA1c value is an underestimate, where the more accurate value adjusted for RBC turnover rate (aHbA1c) of 8.6%, which indicates a higher complication risk for said subject.

In another example, a $k_{age}$ of 0.0077 $day^{-1}$ (or RBC lifespan of 130 days) and a seemingly high measured HbA1c 9% would lead to aHbA1c of 7.1%. The seemingly high measured HbA1c of 9% would indicate a poor glycemic control and significant complication risk. However the person has low complication risk by aHbA1c of 7.1%. Working from the measured HbA1c value of 9%, said subject would likely receive treatment that could the subject at risk for hypoglycemia because the aHbA1c is 7.1%.

When only K is available, aHbA1c can be estimated with Equation 20. For example, when the measured HbA1c is 8% and a high K value of $6\times10^{-4}$ $day^{-1}$ is determined, an aHbA1c estimation of 7%. This adjustment is usually conservative and, therefore, safe to use when $k_{age}$ is not yet available. In this example, unnecessary, and potentially harmful, treatment may be given based on the measured HbA1c value when no treatment should be given based on the aHbA1c value.

In another example, when the measured HbA1c is 7% and a low K value of $4\times10^{-4}$ day$^{-1}$ is determined, the estimated aHbA1c is 8.9%. In this instance, treatment may not be given when relying solely on the measured HbA1c value but should be given because of the high aHbA1c.

The $k^{ref}_{age}$ herein is a predetermined value used as a reference average RBC turnover rate that describes the RBC lifespan. A RBC turnover rate is 1 divided by the RBC lifespan*100 (or $k_{age}$=(1/RBC lifespan)*100) to give $k_{age}$ the units of 1% per day. $k^{ref}_{age}$ is calculated the same way using the desired reference average RBC lifespan.

The $k_{age}$ of a subject can be determined by a variety of methods including, but not limited to, methods described in herein; in US Pat. App. Pub. No. 2018/0235524; in U.S. Prov. Pat. App. No. 62/750,957; and in U.S. Prov. Pat. App. No. 62/939,956; each of which is incorporated herein by reference in their entirety for all purposes.

The HbA1c may be measured in a laboratory and/or calculated (e.g., as described herein as cHbA1c) based, at least in part, on glucose monitoring data. Preferably, said glucose monitoring data is continuous with little to no missed readings to provide higher accuracy in the calculated HbA1c level. Herein, when an HbA1c is described as calculated, the HbA1c level may be referred to in the art as calculate or estimated. Several methods can be used for calculating (or estimating) an HbA1c level including, but not limited to, the eAG/A1C Conversion Calculator provided by the American Diabetes Association; glucose management indicator (GMI) methods (e.g., methods described in *Glucose management indicator (GMI): A new term for estimating A1C from continuous glucose monitoring* Diabetes 41(11): 2275-2280 November 2018); methods described in *Translating the A1C assay into estimated average glucose values* Diabetes Care 31(8):1473-8 Aug. 2008 PMID: 18540046; methods described in *Mechanistic modeling of hemoglobin glycation and red blood cell kinetics enables personalized diabetes monitoring* Sci. Transl. Med. 8, 359ra130 October 2016; US Pat. App. Pub. No. 2018/0235524; U.S. Prov. Pat. App. No. 62/750,957; and U.S. Prov. Pat. App. No. 62/939,956; and the like; and any hybrid thereof. Each of the foregoing patent applications are incorporated herein by reference in their entirety for all purposes.

Methods of the present disclosure include determining (e.g., measuring and/or calculating based on glucose monitoring) a HbA1c level for a subject; determining a RBC elimination rate constant (also referred to as RBC turnover rate and $k_{age}$, typically having units of day$^{-1}$) for the subject; and calculating an adjusted HbA1c value (aHbA1c) for the subject based on the HbA1c level, the $k_{age}$, and a defined reference $k_{age}$ ($k^{ref}_{age}$). Then, the subject may be diagnosed, treated, and/or monitored based on the aHbA1c.

A nonlimiting example method of the present disclosure may comprise: providing (or taking) a plurality of blood glucose measurements for the subject; calculating a HbA1c for the subject based, at least in part, on the plurality of blood glucose measurements; providing (or determining) a $k_{age}$ for a subject; and calculating an aHbA1c for the subject based on the HbA1c level, the $k_{age}$, and a $k^{ref}_{age}$. Then, the subject may be diagnosed, treated, and/or monitored based on the aHbA1c.

Another nonlimiting example method of the present disclosure may comprise: providing (or measuring) an HbA1c for a subject based; providing (or determining) a $k_{age}$ for a subject; and calculating an aHbA1c for the subject based on the HbA1c level, the $k_{age}$, and a $k^{ref}_{age}$. Then, the subject may be diagnosed, treated, and/or monitored based on the aHbA1c.

Personalized-Target Glucose Range and Personalized Glucose Level

Typically, the glucose levels in subjects with diabetes is preferably maintained between 70 mg/dL and 180 mg/dL. However, the kinetic model described herein illustrates that the intra-cellular glucose levels are dependent on physiological parameters like $k_{gly}$. Further, the intra-cellular glucose level is associated with hypoglycemia and hyperglycemia damage to organs, tissues, and cells. Therefore, a measured glucose level may not actually correspond to the actual physiological conditions that relevant to diabetes management in a subject. For example, a subject with a higher than normal $k_{gly}$ uptakes glucose more readily into cells. Therefore, a 180 mg/dL measured glucose level may be too high for the subject and, in the long run, further continue the subject's diabetes. In another example, a subject with a lower than normal $k_{gly}$ uptakes glucose to a lesser degree into cells. Accordingly, at a 70 mg/dL glucose level, the subject's intracellular glucose level may be much lower making the subject feel weak and, in the long term, lead to the subject being hypoglycemic.

Herein, three methods are presented for taking into account a subject's specific $k_{gly}$ with respect to a glucose reading and/or a corresponding personalized glucose range: (a) adjusting the accepted normal glucose upper and lower limits to arrive at a personalized-target glucose range that is based on $k_{gly}$, (b) adjusting a subject's measured glucose level to an effective plasma glucose level that correlates to the accepted normal glucose upper and lower limits, and (c) adjusting a subject's measured glucose level to an intracellular glucose level that correlates to an accepted normal lower intracellular glucose limit (LIGL) and the an normal upper intracellular glucose limit (UIGL).

First, using the accepted normal lower glucose limit (LGL) and the accepted normal glucose upper limit (AU), equations for a personalized lower glucose limit (GL) (Equations 21 and 22) and a personalized upper glucose limit (GU) (Equations 23 and 24) can be derived. Equations 22 and 24 are Equations 21 and 23 rewritten for when both a measured HbA1c and an aHbA1c are available.

$$GL = \frac{K_M * LGL}{\frac{k_{gly}^{sub}}{k_{gly}^{ref}} * K_M + LGL\left(\frac{k_{gly}^{sub}}{k_{gly}^{ref}} - 1\right)} \quad \text{Equation 21}$$

where $k_{gly}^{ref}$ is the $k_{gly}$ for a normal person and $k_{gly}^{sub}$ is the subject's $k_{gly}$ $$GL = \frac{K_M * LGL * HbA1c(1 - aHbA1c)}{aHbA1c(1 - HbA1c) * K_M + LGL(aHbA1c - HbA1c)} \quad \text{Equation 22}$$

$$GU = \frac{K_M * AU}{\frac{k_{gly}^{sub}}{k_{gly}^{ref}} * K_M + AU\left(\frac{k_{gly}^{sub}}{k_{gly}^{ref}} - 1\right)} \quad \text{Equation 23}$$

$$GU = \frac{K_M * AU * HbA1c(1 - aHbA1c)}{aHbA1c(1 - HbA1c) * K_M + AU(aHbA1c - HbA1c)} \quad \text{Equation 24}$$

Equations 21 and 23 are based on $k_{gly}$ because the higher and lower limits of a glucose range are based on an equivalent intracellular glucose level.

The currently accepted values for the foregoing are LGL=70 mg/dL, $k_{ref}^{gly}$=6.2*$10^{-6}$ dL*$mg^{-1}$*$day^{-1}$, and AU=180 mg/dL.

Figure 4A:
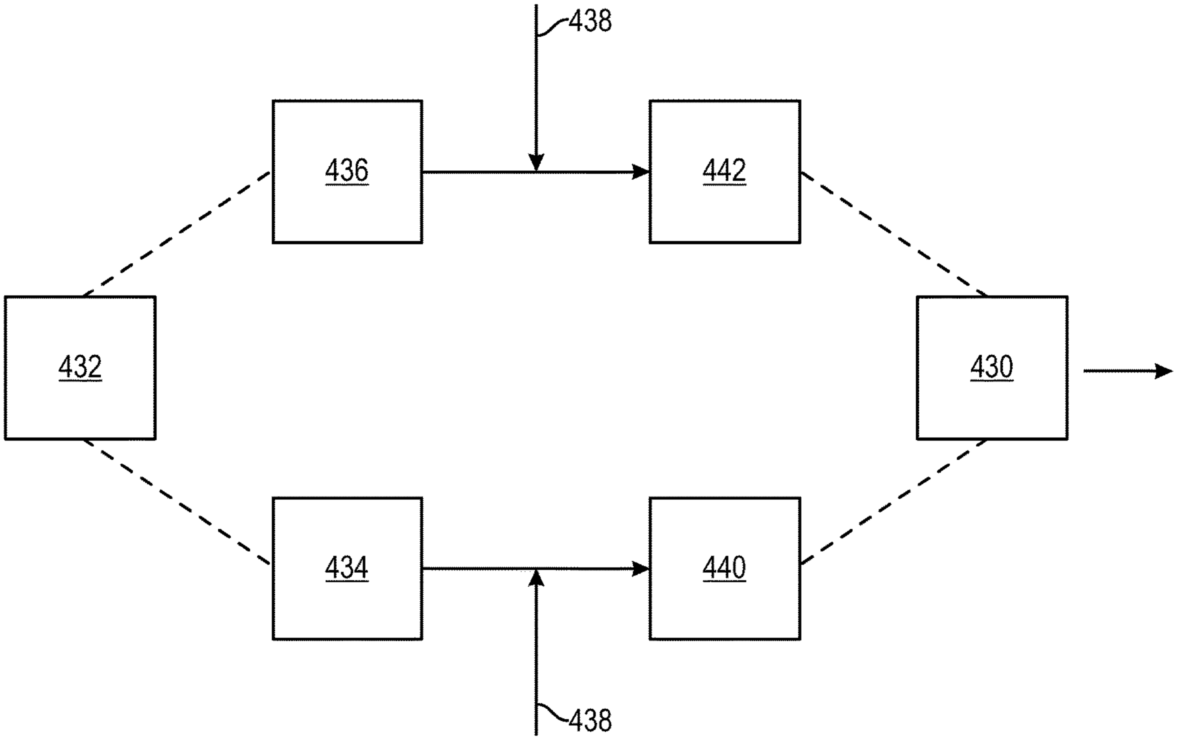
FIG. 4A illustrates an example of a method of determining a personalized-target glucose range in accordance with some of the embodiments of the present disclosure.

FIG. 4A illustrates an example of a method of determining a personalized-target glucose range 430. A desired glucose range 432 (e.g., the currently accepted glucose range) having a lower limit 434 and an upper limit 436 can be personalized using physiological parameter $k_{gly}$ 438 using Equation 21 and Equation 23, respectively. This results in a personalized lower glucose limit (GL) 440 (Equation 21±7%) and a personalized upper glucose limit (GU) 442 (Equation 23±7%) that define the personalized-target glucose range 430. Alternatively or in addition to the foregoing, a desired glucose range 432 (e.g., the currently accepted glucose range) having a lower limit 434 and an upper limit 436 can be personalized using a measured HbA1c and aHbA1c 438 using Equation 22 and Equation 24, respectively. Therefore, methods may generally include, after (a) calculating $k_{gly}$ and/or (b) after measuring HbA1c and calculating aHbA1c, a personalized-target glucose range may be determined where the lower glucose limit may be altered according to Equation 21 (and/or Equation 22)±7% and/or the upper glucose limit may be altered according to Equation 23 (and/or Equation 24)±7%. For example, a subject with a $k_{gly}$ of 5.5*$10^{-6}$ dL*$mg^{-1}$*$day^{-1}$ may have a personalized-target glucose range of about 81±7 mg/dL to about 219±27 mg/dL. Therefore, the subject may have a different range of acceptable glucose levels than the currently practiced glucose range.

Figure 4B:
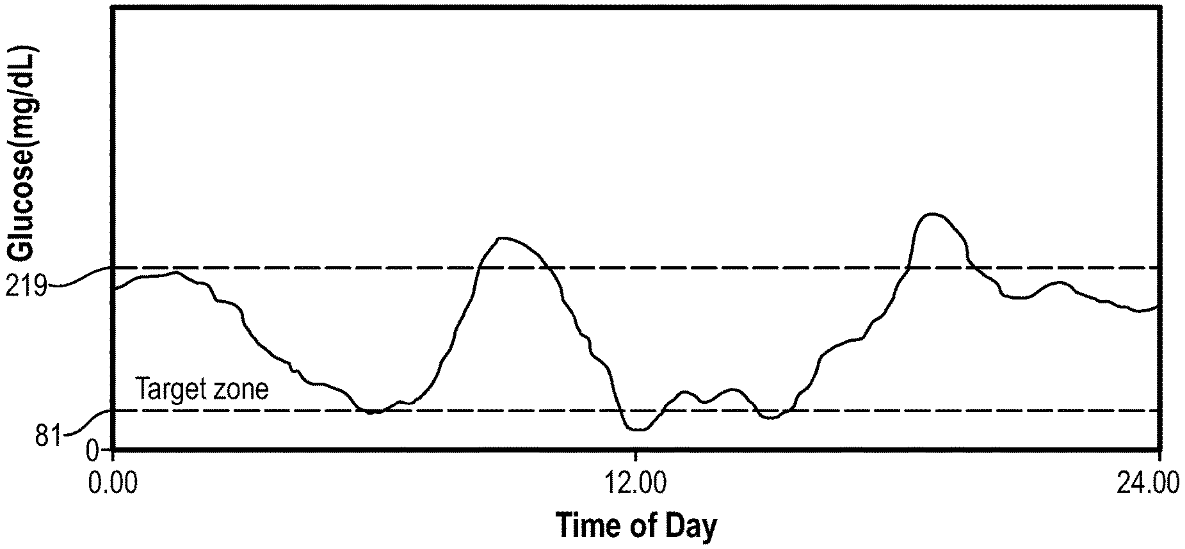
FIG. 4B illustrates an example of a personalized-target glucose range report that may be generated as an output by a system in accordance with some of the embodiments of the present disclosure.

FIG. 4B, with reference to FIG. 2, illustrates an example of a personalized-target glucose range report that may be generated as an output 218 by a physiological parameter analysis system 210 of the present disclosure. The illustrated example report includes a plot of glucose level over a day relative to the foregoing personalized-target glucose range (shaded area). Alternatively, other reports may include, but are not limited to, an ambulatory glucose profile (AGP) plot, a numeric display of the personalized-target glucose range with the most recent glucose level measurement, and the like, and any combination thereof.

In another example, a subject with a $k_{gly}$ of 6.5*$10^{-6}$ dL*$mg^{-1}$*$day^{-1}$ may have a personalized-target glucose range of about 66±5.5 mg/dL to about 167±18 mg/dL. With the much-reduced upper glucose level limit, the subject's personalized diabetes management may include more frequent glucose level measurements and/or medications to stay substantially within the personalized-target glucose range.

In yet another example, a subject with a $k_{gly}$ of 5.0*$10^{-6}$ dL*$mg^{-1}$*$day^{-1}$ may have a personalized-target glucose range of about 92±8 mg/dL to about 259±34 mg/dL. This subject is more sensitive to lower glucose levels and may feel weak, hungry, dizzy, etc. more often if the currently practiced glucose range (70 mg/dL and 180 mg/dL) were used.

While the foregoing example all include a personalized glucose lower limit and a personalized glucose upper limit, personalized-target glucose range may alternatively include only the personalized glucose lower limit or the personalized glucose upper limit and use the currently practiced glucose lower or upper limit as the other value in the personalized-target glucose range.

In a second method for taking into account a subject's specific $k_{gly}$ with respect to a glucose reading and/or a corresponding personalized glucose range, a subject's plasma glucose level (e.g., as measured with an analyte sensor configured to measure a glucose level in a bodily fluid where said sensor may be a part of a larger system) is personalized to yield an effective plasma glucose ($PG_{eff}$) level using $k_{gly}$ per Equation 16.

$$PG_{eff} = \frac{r * PG * K_M}{K_m + (1 - r)PG} \quad \text{Equation 16}$$

where $$r = \frac{k_{gly}}{k_{gly}^{ref}}$$

The $PG_{eff}$ level may be used in combination with the accepted normal lower glucose limit and/or the accepted normal glucose upper limit for diagnosing, monitoring, and/or treating a subject. That is, the $PG_{eff}$ level is interpreted relative to the accepted glucose limits, which herein are considered between 70 mg/dL and 180 mg/dL but may change based on new clinical and/or scientific data and health officials' recommendations.

For example, a subject with a $k_{gly}$ of 6.5*$10^{-6}$ dL*$mg^{-1}$*$day^{-1}$ may receive a measured glucose level of 170 mg/dL that, when Equation 16 is applied changes to 183 mg/dL, which is interpreted in context of the accepted glucose limits (70 mg/dL to 180 mg/dL). Therefore, currently, the subject would consider the measurement of 170 mg/dL to be within accepted limits. However, the effective plasma glucose is actually higher, which may impact the proper dose of insulin or other medication that should be delivered.

In a third method for taking into account a subject's specific $k_{gly}$ with respect to a glucose reading and/or a corresponding personalized glucose range, a subject's plasma glucose level (e.g., as measured with an analyte sensor configured to measure a glucose level in a bodily fluid where said sensor may be a part of a larger system) is personalized to an intracellular glucose (IG) level using $k_{gly}$ per Equation 17.

$$IG = \frac{k_{gly} * PG}{k_g\left(1 + \frac{PG}{K_M}\right)} \quad \text{Equation 17}$$

The subject's IG level may then be compared to an accepted normal lower intracellular glucose limit (LIGL) and an accepted normal upper intracellular glucose limit (UIGL). The currently accepted values for LIGL and UIGL are 0.29 mg/dL and 0.59 mg/dL, respectively.

The personalized-target glucose range and/or personalized glucose level (e.g., an effective plasma glucose level or an intracellular glucose level) may be determined and/or implemented in a physiological parameter analysis system. For example, a set of instructions or program associated with a glucose monitor and/or health monitoring device that determines a therapy (e.g., an insulin dosage) may use a personalized-target glucose range and/or personalized glucose level in such analysis. In some instances, a display or subject interface with display may display the personalized-target glucose range and/or personalized glucose level.

The personalized-target glucose range and/or personalized glucose level may be updated over time as one or more physiological parameters are recalculated.

The personalized-target glucose range may be determined and/or implemented in a physiological parameter analysis system. For example, a set of instructions or program associated with a glucose monitor and/or health monitoring device that determines a therapy (e.g., an insulin dosage) may use a personalized-target glucose range in such analysis. In some instances, a display or subject interface with display may display the personalized-target glucose range.

The personalized-target glucose range may be updated over time as one or more physiological parameters are recalculated.

Personalized-Target Average Glucose

Equation 27 can be used to calculate a personalized-target average glucose level (GT) from a reference glucose target RG. The reference target glucose can take any value that physician determines suitable, for example 120 mg/dL.

$$GT = \frac{K_M * RG}{\frac{k_{gly}^{sub}}{k_{gly}^{ref}} K_M + RG\left(\frac{k_{gly}^{sub}}{k_{gly}^{ref}} - 1\right)} \quad \text{Equation 27}$$

Alternatively or in combination with Equation 27, Equation 28 can be used to calculate a GT based on a measured HbA1c and an aHbA1c.

$$GT = \frac{K_M * RG * HbA1c(1 - aHbA1c)}{aHbA1c(1 - HbA1c) * K_M + RG(aHbA1c - HbA1c)} \quad \text{Equation 28}$$

Alternatively or in combination with Equations 27 and/or 28, Equation 29 can be used to calculate a GT when the target HbA1c value (AT) is known.

$$GT = AT/(K(1-AT)) \quad \text{Equation 29}$$

In some embodiments, a physiological parameter analysis system may determine an average glucose level for the subject during time period 208 and, optionally, display the average glucose level and/or the target average glucose level. The subject may use the current average glucose level and the target average glucose level to self-monitor their progress over time period 208. In some instances, the current average glucose level may be transmitted (periodically or regularly) to a health care provider using a physiological parameter analysis system for monitoring and/or analysis.

Figure 5:
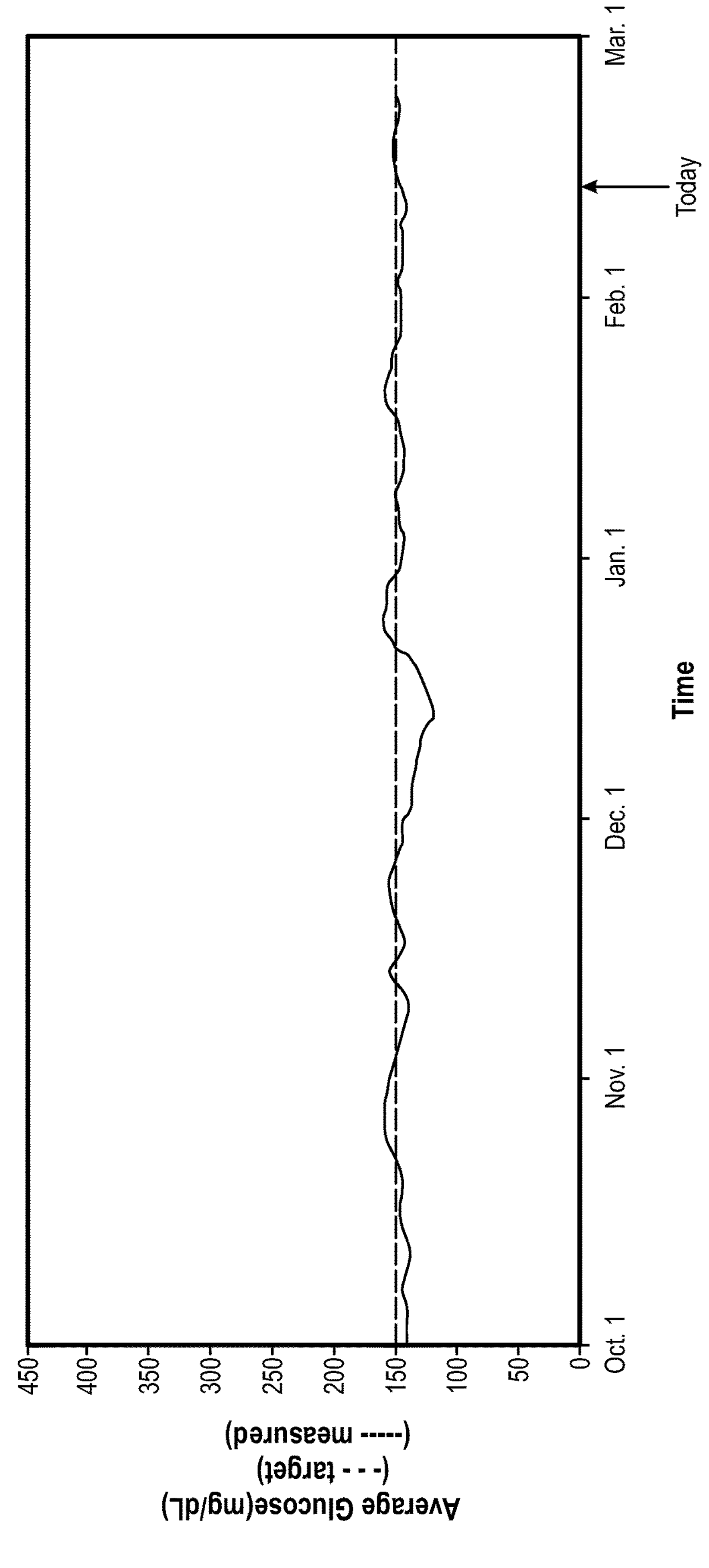
FIG. 5 illustrates an example of a personalized-target average glucose report that may be generated as an output by a system in accordance with some of the embodiments of the present disclosure.

FIG. 5, with reference to FIG. 2, illustrates an example of a personalized-target average glucose report that may be generated as an output 218 by a physiological parameter analysis system 210 of the present disclosure. The illustrated example report includes a plot of a subject's average glucose (solid line) over time and the personalized-target average glucose (illustrated at 150 mg/dL, dashed line). Alternatively, other reports may include, but are not limited to, a numeric display of the personalized-target average glucose with the subject's average glucose level over a given time frame (e.g., the last 12 hours), and the like, and any combination thereof.

The personalized-target average glucose level may be updated over time as updated relevant physiological parameters, calculated values, and/or measured values for one or more of Equations 27-29 are obtained.

Personalized Treatment—Subject Triage

Insulin pumps along with continuous glucose monitoring may be used for subjects that need tight control of their glucose levels. As illustrated above, the target glucose range is individualized and based on $k_{gly}$. Therefore, in some instances, subjects with a narrower personalize-target glucose range may be stronger candidates for insulin pumps with continuous monitoring. Triage of subjects to be stronger candidates for insulin pumps along with continuous glucose monitoring may be based on a spread of the personalized-target glucose range, and $k_{gly}$.

The spread between currently practiced glucose lower or upper limit is about 110 mg/dL. However, as illustrated above, depending on $k_{gly}$ could narrow to about 60 mg/dL or less. Some embodiments may involve triaging a subject to an insulin pump with continuous glucose monitoring when the personalized-target glucose range span is below a threshold that is less than 110 mg/dL.

Some embodiments may involve triaging a subject to an insulin pump with continuous glucose monitoring when $k_{gly}$ exceed a threshold greater than $6.2*10^{-6}$ $dL*mg^{-1}*day^{-1}$.

Some embodiments may involve placing a subject to intense hypoglycemia prevention program when $k_{gly}$ is lower than a threshold, e.g. $6.2*10^{-6}$ $dL*mg^{-1}*day^{-1}$.

In some embodiments, triaging a subject to an insulin pump with continuous glucose monitoring may be a stepped triage where first a subject's glucose levels are monitored continuously for a reasonable time period (e.g., about 5 days, about 10 days, about 15 days, about 30 days, or more). This continuous monitoring time period can be used to assess if the subject is capable of managing glucose levels effectively or if an insulin pump is better, or required.

Whether the triaging is straight to an insulin pump with continuous glucose monitoring or a stepped triage with monitoring before treatment with the insulin pump may be determined by the level of the indicators (i.e., the personalized-target glucose range span, $k_{gly}$, or any combination thereof). For example, if $k_{gly}$ is about $6.4*10^{-6}$ $dL*mg^{-1}*day^{-1}$ and the personalized-target glucose range span is about 103 mg/dL, the subject may be more suited for a stepped triage as compared to another subject where the corresponding indicators suggest an insulin pump should be used.

In some embodiments, triage may be based on a lookup table (e.g., stored in a physiological parameter analysis system of the present disclosure). The lookup table may, for example, correlate multiple values to each other including, but not limited to, one or more physiological parameters ($k_{gly}$, $k_{age}$, and/or K), a personalized-target glucose range span, and/or other factors described herein like an existing medical condition, a family history of a medical condition, a current treatment, an age, a race, a gender, a geographic location, a diabetes type, a duration of diabetes diagnosis, and the like, and any combination thereof. Columns in the lookup table may, for example, define ranges or limits for the foregoing parameters, and the rows may indicate a suggested course of action, which may be an output 218 of a physiological parameter analysis system 210 of FIG. 2. For example, two columns may define an upper and lower bound of $k_{gly}$, where each row corresponds to a suggested course of action, such as "candidate for insulin pump," "candidate for closed-loop control system," "candidate for basal/bolus insulin therapy," "candidate for basal only insulin therapy," or any such treatment used to control diabetes or effect the subject's glycation. In some instances, more than one course of action may be indicated. Therefore, in this example, a subject triage report may simply display the suggested course(s) of action.

Alternatively, the subject triage report may, for example, show a map of zones corresponding to the course(s) of action on a plot defined by one or more of the parameters described above relative to the lookup table. Such zones may, in some instances, be defined by the lookup table, labeling each zone representing a recommendation and indicated the glycemic parameter point on the map to show the relevant zone for that subject.

While the two foregoing subject triage reports are examples based on lookup tables, alternatively, the two foregoing subject triage reports could be based on other correlations between (1) one or more physiological parameters ($k_{gly}$, $k_{age}$, and/or K), a personalized-target glucose range span, and/or other factors described herein and (2) a course(s) of action (e.g., a mathematical algorithm or matrix analysis).

As described, a subject's glycation parameters may help healthcare providers and payors to better determine what therapy tools are most appropriate for which subjects. For instance, closed-loop insulin pump systems are expensive to employ and maintain, but subjects who have a high glycation rate may have a very narrow personalized-target glucose range where the safest treatment is keeping their glucose levels within such ranges using a closed-loop insulin pump system.

In some embodiments, the insulin pumps along with continuous glucose monitoring may be closed-loop systems. In some embodiments, the insulin pumps along with continuous glucose monitoring may be hybrid-loop systems. For example, referring back to FIG. 3, a physiological parameter analysis system may further include one of the foregoing insulin pumps communicable with one or more of the components in the physiological parameter analysis system 310, for example, the glucose monitor 324 (e.g., a continuous glucose monitoring system) and health monitoring device 320.

Personalize Treatment—Titration of Diabetes Medication

In some embodiments, one or more physiological parameters ($k_{gly}$, $k_{age}$, and K) may be used in titrating dosages of diabetes medication (e.g., insulin) to a subject. For example, referring to FIG. 2, a physiological parameter analysis system 210 of the present disclosure may determine or have input (1) one or more physiological parameters, (2) a personalized-target glucose range, (3) a personalized glucose level (e.g., an effective plasma glucose level or an intracellular glucose level), and/or (4) a personalized-target average glucose. Then, when a subsequent glucose level is measured the physiological parameter analysis system 210 may output a recommended diabetes medication dosage. An alternative or complimentary output 218 may be a glucose pattern insight report.

Examples of glucose pattern insight reports can be found in US Patent Application Publication Nos. 2014/0188400 and 2014/0350369, each incorporated herein by reference. The disclosed analyses and reports in the forgoing applications may be modified based on the one or more physiological parameters ($k_{gly}$, $k_{age}$, and K) of the present disclosure.

Figure 6:
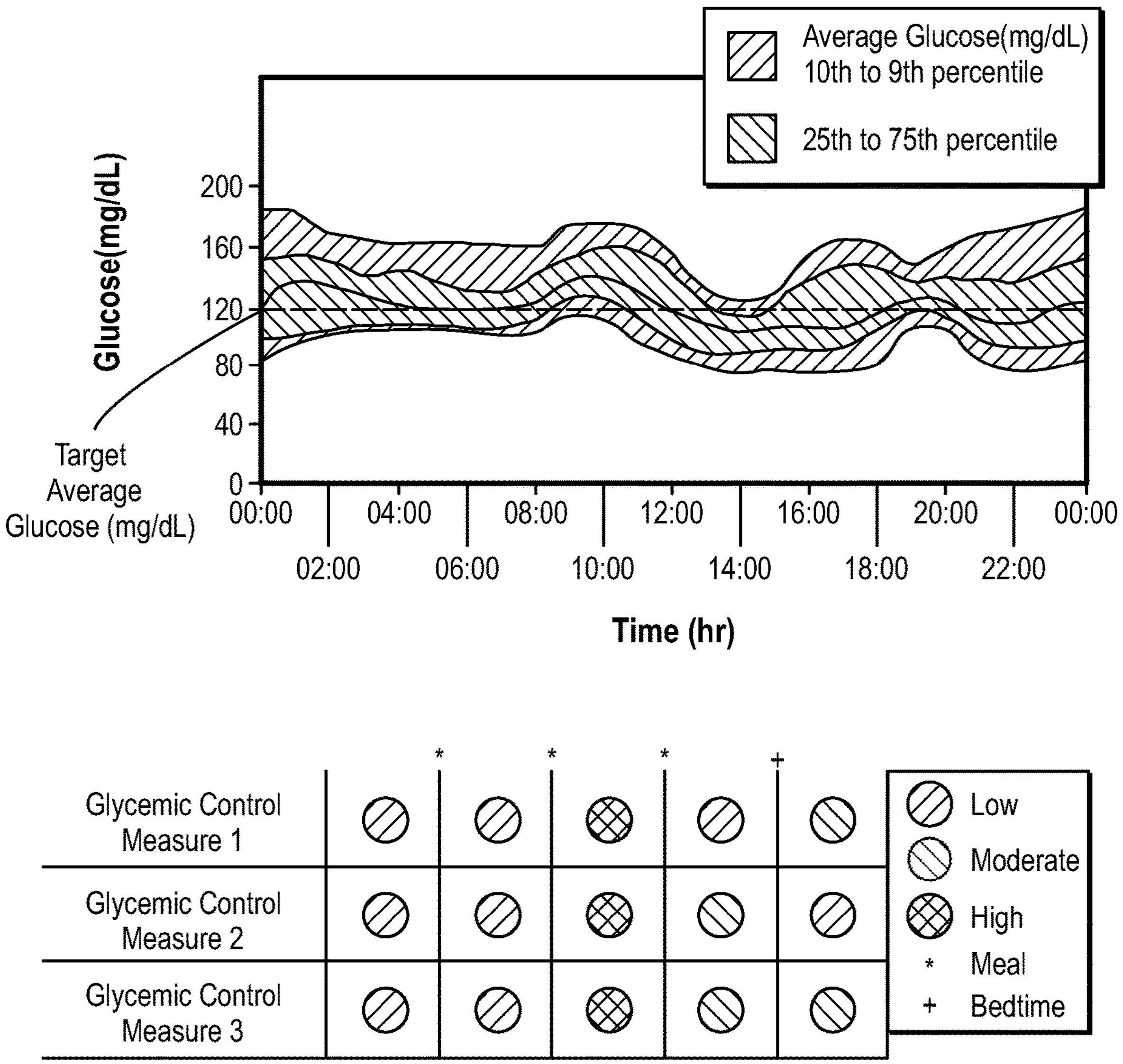
FIG. 6 illustrates an example of a glucose pattern insight report that may be generated as an output by a system in accordance with some of the embodiments of the present disclosure.

For example, FIG. 6, with reference to FIG. 2, illustrates an example of a glucose pattern insight report that may be an output 218 of a physiological parameter analysis system 210 (e.g., an insulin titration system). The illustrated glucose pattern insights report incorporates an AGP along with a table of glycemic control measures (or "traffic lights"). As illustrated, the report includes an AGP plot over an analysis time period (e.g., about one to about four months) that illustrates the personalized-target average glucose at 120 mg/dL, the average glucose levels for the subject over the analysis time period, the $25^{th}$ to $75^{th}$ percentile of glucose levels for the subject over the analysis time period, and the $10^{th}$ to $90^{th}$ percentile of glucose levels for the subject over the analysis time period. Optionally, the glucose pattern insight report may further or alternatively display the personalized-target glucose range and/or personalized glucose level (e.g., an effective plasma glucose level or an intracellular glucose level) relative to the currently accepted glucose range. Additionally, the glucose pattern insight report may optionally further include one or more of: a measured HbA1c level, a cHbA1c level, an adjusted HbA1c level based on either laboratory HbA1c or glucose data, the date range over which the average glucose and related percentiles were determine, and the like.

Below the AGP plot on the glucose pattern insight report is the table that correlates one or more (illustrated as three) glycemic control measures to a subject's average glucose levels for a given shortened time period of the day over the analysis time period. The correlation displays, in this example, as traffic lights (e.g., green (good), yellow (moderate), or high (red)) that correspond to the risk of a condition based on the glycemic control measures. Examples of glycemic control measures include, but are not limited to, likelihood of low glucose, likelihood of high glucose, the proximity of the average glucose to the personalized-target average glucose, the adherence of the glucose levels to the personalized-target glucose range and/or the personalized glucose level relative to the currently accepted glucose range, the degree of variability of the average glucose below (or above) to the personalized-target average glucose, the degree of variability of the glucose levels outside (below and/or above) the personalized-target glucose range, and/or the personalized glucose level relative to the currently accepted glucose range and the like.

In some embodiments, the glucose pattern insights report may be used as part of a diabetes medication titration system, where the traffic lights (or values associated therewith) can drive logic to provide treatment modifications such as changing basal dosages of the diabetes medication or bolus amounts of the diabetes medication associated with meals. For example, when used in conjunction with an automatic or semi-automatic system for titration, the logic driving these traffics lights may provide recommendations to subjects on dosage adjustments.

The glucose pattern insights report and related analyses that incorporate the use of the kinetic model described herein may provide better treatment to subjects with diabetes. For this example, as described above, a subject with a $k_{gly}$ of $5.1*10^{-6}$ $dL*mg^{-1}*day^{-1}$ may have a personalized-target glucose range of about 90±8 mg/dL to about 250±32 mg/dL. This subject is more sensitive to lower glucose levels and may feel weak, hungry, dizzy, etc. more often if the currently practiced glucose range (70 mg/dL and 180 mg/dL) were used. The analytical logic used for the glucose pattern insights report described herein that uses one or more physiological parameters ($k_{gly}$, $k_{age}$, and K) may include settings that define the risk of hypoglycemia as traffic lights for "likelihood of low glucose." For example, if the likelihood of low glucose indicates low risk (e.g., a green traffic light), then it is considered safe to increase insulin. If the likelihood of low glucose indicates moderate risk (e.g., yellow traffic light), then it is considered that the current risk is acceptable but no further increase of insulin should be made. Finally, if the likelihood of low glucose indicates high risk, then it is recommended that insulin should be reduced to get the glucose back to tolerable levels. For a subject with high risk of hypoglycemia because of an increase lower glucose level threshold, the amount of risk associated with moderate and high risk (e.g., how far below the lower glucose level threshold) may be less than a subject with a normal lower glucose level threshold.

While the foregoing example discusses a glucose pattern insights report as the output 218, other outputs using the same logic and analyses may be used in other embodiments. For example, the output 218 may be values of dosage recommendations.

The one or more physiological parameters ($k_{gly}$, $k_{age}$, and K) and related analyses (e.g., personalized-target glucose range, personalized glucose level, personalized-target average glucose, cHbA1c, aHbA1c, and the like) may be updated periodically (e.g., about every 3 months to annually). The frequency of updates may depend on, among other things, the subject's glucose level and diabetes history (e.g., how well the subject stays within the prescribed thresholds), other medical conditions, and the like.

An insulin titration system may optionally also utilize error associated with the one or more physiological parameters ($k_{gly}$, $k_{age}$, and K). Error values can be determine using standard statistically techniques by those skilled in the art and may be used as another set of parameters for configuring the titration system. For example, the titration system may use the reduced amount of risk for hypoglycemia (i.e., a smaller tolerance to be below the lower glucose level threshold for indicating moderate and high risk) may be implemented when the lower glucose level of the personalized-target glucose range of about 75 mg/dL with an error of about 7% or less.

The dosage of diabetes mediation (e.g., via titration) may be updated over time as one or more physiological parameters are recalculated.

Closed-Loop and Hybrid Closed-Loop Control Systems

Closed-loop systems and hybrid closed-loop systems that recommend or administer insulin dosages to a subject have been developed for insulin delivery based on near real-time glucose readings. These systems are often based on models describing the subject's physiology, glucose sensor dynamics, and glucose sensor error characteristics. In some embodiments, the one or more physiological parameters ($k_{gly}$, $k_{age}$, and K) and related analyses (e.g., personalized-target glucose range, personalized glucose level, personalized-target average glucose, cHbA1c, aHbA1c, and the like) may be incorporated into the closed-loop system, similarly to what was described above for insulin titration, in order to better meet the needs of the subject.

Closed-loop systems often are configured to "drive" the subject's glucose levels inside a target range and/or toward a single glucose target, which may be the personalized-target glucose range, the personalized glucose level relative to the accepted target glucose range, and/or the personalized-target average glucose described herein. For example, for a subject with high $k_{gly}$ and an increased lower glucose limit for their personalized-target glucose range, the controller may drive their glucose levels in a way to stay above the lower glucose limit based on $k_{gly}$, which avoids lower glucose levels that adversely affect them more than subjects with a normal glucose range. Similarly, subjects with reduced upper glucose limits for their personalized-target glucose range may have the controller of a closed-loop insulin delivery system and hybrid closed-loop insulin delivery system drive glucose to stay below the personalized-upper glucose limit to mitigate hyperglycemic effects.

The metrics by which a closed-loop insulin delivery system and hybrid closed-loop insulin delivery system determine a dosage of insulin may be updated over time as one or more physiological parameters are recalculated. For example, the personalized-target glucose range, personalized glucose level, and/or personalized-target average glucose may be updated when one or more physiological parameters are recalculated.

Personalized Treatment—Glycation Medication

Diabetes is a disease caused by a subject's pancreas being unable to produce sufficient (or any) insulin. However, in some instances, a subject's glycation process may be the source of the body not properly controlling intracellular glucose. Such subjects may be more responsive to treatments that use glycation medications rather than traditional diabetes treatments. The kinetic model of the present disclosure derives $k_{gly}$ and/or K (which is based in part on $k_{gly}$). Therefore, one or both of these physiological parameters may be used in identifying, treating, and/or monitoring a subject with a glycation disorder.

Some embodiments may involve monitoring $k_{gly}$ and/or K for a subject on glycation medication and, optionally, changing a glycation medication dosage based on changes to $k_{gly}$ and/or K.

In some embodiments, an output 218 of the physiological parameter analysis system 210 of FIG. 2 may be a glycation medication report that includes glycation medication and/or dosage recommendations based on $k_{gly}$ and/or K calculated by the physiological parameter analysis system 210. This output 218 may be displayed for a subject, healthcare provider, and/or the like to review and adjust the glycation medication and/or dosage.

Alternatively, the dosage recommendations provide a subject and/or automated medication delivery system with the next dosage to be administered. Here, the system guides titration of the medication, where the subject may start with the lowest dosage or a recommended initial dosage. The initial dosage may be defined by the current condition of the subject, the subject's $k_{gly1}$ and/or $K_1$, and other factors described herein. After an appropriate amount of time has passed for the effects of the current medication dosage to be adequately determined, $k_{gly2}$ and/or $K_2$ can be determined based on a new measured HbA1c level and the glucose levels measured during the medication dosage. $k_{gly2}$ and/or $K_2$ may then be compared to (1) $k_{gly1}$ and/or $K_1$ and/or (2) a target $k_{gly}$ and/or a target K to determine if the dosage needs to be changed. For example, for a high glycator subject taking a medication is intended to lower glycation rate, if $k_{gly2}$ is still higher than desired, then the dosage recommendation may be increased according to (1) standard titration protocols and/or (2) a system that accounts for how past dosage changes affect the subject (known as control theory). In another example, if the subject's $k_{gly2}$ is low, then the dosage may be decreased. Medications could also be similarly titrated to affect K or other parameters. In addition, a similar process could be used to recommend non-medication treatments such as blood transfusion or harvesting by guiding the appropriate amount of blood to be affected.

Using $k_{gly}$ and/or K to monitor glycation medication efficacy and titration is valuable to healthcare providers for treating subjects with abnormal glycation physiology.

The metrics by which a dosage of glycation medication is determined may be updated over time as one or more physiological parameters are recalculated.

Identifying Abnormal or Diseased Physiological Condition

The kinetic modeling, in certain embodiments, provides physiological parameters (e.g., $k_{gly}$, $k_{age}$ (or $k_{gen}$), and/or K) for different time periods, where the same parameter is compared between the different time periods to indicate abnormal or disease state of the subject. Variation in the $k_{gly}$, $k_{age}$, and/or K in subjects may provide an indication of abnormal or disease condition of the subject. That is, while $k_{gly}$, $k_{age}$, and/or K varies between subjects, a variation in $k_{gly}$, $k_{age}$, and/or K for a single individual are small and slow. Thus, a comparison of $k_{gly}$, $k_{age}$, and/or K at two or more different time periods provides physiological condition information of the subject. For example, when a clinically significant change to $k_{gly}$, $k_{age}$, and/or K is observed over time an abnormal or diseased physiological condition may, and likely, exists.

For example, when $k_{gly}$ significantly varies over time such that the variation is clinically significant, such clinically significant variation can indicate that the glucose transporter level or cell membrane has changed. Such biological changes may indicate a potential metabolic change in the subject's body resulting from the subject's physiology under-going a disease state.

When $k_{age}$ and/or $k_{gen}$ varies significantly over time such that the variation is clinically significant, such clinically significant variation can indicate changes to the subject's immune system because the immune system is designed to recognize cells that need to be removed.

A clinically significant variation in $k_{age}$ and/or $k_{gen}$ may also or alternatively be associated with the oxygen sensing mechanism in the body. An increasing $k_{age}$ and/or $k_{gen}$ over time may indicate that the subject's body needs the red blood cells to carry more oxygen or the oxygen sensing mechanism is not functioning correctly, either reason indicating a physiological state change such as for example, blood loss or a disease condition.

In yet another example (in combination or alternative of the foregoing examples), clinically significant variation in $k_{age}$ and/or $k_{gen}$ may be associated with bone marrow changes. For example, if the bone marrow suddenly produces a lot more oxygen carrying red blood cells, the subject's body will respond by killing off or eliminating more red blood cells. That is, a clinically significant increase in $k_{age}$ and/or $k_{gen}$ may be associated with bone marrow abnormality.

In another example, a hormone disorder can cause a clinically significant variation in $k_{age}$, $k_{gen}$, and K. Hormones can affect heart rate, contraction strength, blood volume, blood pressure, and red blood cell production. Stress hormones such as catecholamines and cortisol stimulate the release of reticulocytes from the bone marrow and possibly also enhance erythropoiesis. Therefore, large fluctuation on hormone level can change $k_{age}$ and/or $k_{gen}$, and consequently K.

In yet another example, deviations from normal of the $k_{gly}$, $k_{age}$, and/or K may be an indicator of diabetes or pre-diabetes. Using $k_{gly}$, $k_{age}$, and/or K to measure diabetes or pre-diabetes may be more effective than standard fasting glucose tests and measured HbA1c. For instance, a subject with a measured HbA1c value in the normal range and normal fasting glucose may have low $k_{gly}$ associated with high glucose values at times in the day other than fasting. Therefore, the subject may be a candidate for earlier diabetes intervention that otherwise may have gone unnoticed based on standard diabetes diagnoses methods.

In another example, for a subject with a newly high measured HbA1c, the standard diabetes treatments may be employed to lower their HbA1c. However, determining that $k_{gly}$ is abnormal may be an indication that the problem with their glycation physiology rather than their pancreas, suggesting other more targeted forms of treatment.

Embodiments of the present disclosure include displaying the determined $k_{gly}$, $k_{age}$, and/or K, the changes in $k_{gly}$, $k_{age}$, and/or K over time, and/or possible abnormal or diseased physiological conditions.

In the manner described herein, in accordance with the embodiments of the present disclosure, the physiological parameter analysis provides an indication of a subject's abnormal or disease condition, as well as an analysis and/or monitoring tool for one or more parameters or characteristics for a subject's personalized diabetes management.

Identifying Supplements and/or Medicines

Several supplements and medications interact with the kinetics of red blood cell hemoglobin glycation, elimination, and generation within the body. For example, supplements and medicines used by athletes to dope include, but are not limited to, human growth hormones, supplements and medicines that increase metabolic levels, and the like. Human growth hormones can increase red blood cell count and, consequently, increase $k_{age}$. In another example, supplements and medicines that increase metabolic levels (e.g., exercise mimetics like AMPK agonists) can affect $k_{gly}$. Therefore, some embodiments may use one or more physiological parameters ($k_{gly}$, $k_{age}$, and/or K) as an indicator of doping.

In a first example, having one or more physiological parameters ($k_{gly}$, $k_{age}$, and/or K) outside normal ranges may be used, in some instances, as an indicator of doping.

In another example, once the one or more physiological parameters ($k_{gly}$, $k_{age}$, and/or K) are determined, continuous monitoring over a 10-day or longer period could identify sudden changes in the physiological parameters that could indicated doping. This could be used alone or in combination with the foregoing example of the one or more physiological parameters being outside normal ranges.

Physiological Age

The physiological parameters $k_{age}$ and, consequently, K change due to aging. Therefore, $k_{age}$ and/or K (provided a stable or known change in $k_{gly}$) may be used as biological markers to calculate a standardized metabolic age. Generally, over time, $k_{age}$ decreases and K increases. Using a correlation between $k_{age}$ and/or K and age in healthy subjects, a new subject's metabolic age may be calculated. This metabolic age may then be used as an indicator of the new subject's risk for age-related degenerative conditions like heart disease, Alzheimer's, or osteoperosis. The risk for age-related degenerative conditions may be used in conjunction with family history of age-related degenerative conditions for proactive screening and/or preventive treatment. For example, a 54-year old subject with a metabolic age of 65 with a family history of cardiovascular disease developing later in life may be tested more often for signs and/or progression of cardiovascular disease than a 54-year old subject with a metabolic age of 50 and a similar family history.

Analyte Monitors and Monitoring Systems

Generally, embodiments of the present disclosure are used with or as systems, devices, and methods for measuring glucose and, optionally, at least one other analyte in a bodily fluid. The embodiments described herein can be used to monitor and/or process information regarding glucose and, optionally, at least one other analyte. Other analytes that may be monitored include, but are not limited to, glucose derivatives, HbA1c, reticulocyte count, RBC GLUT1 level, acetyl choline, amylase, bilirubin, cholesterol, chorionic gonadotropin, creatine kinase (e.g., CK-MB), creatine, creatinine, DNA, fructosamine, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor glucose and one or more than one analytes, each of the analytes may be monitored at the same or different times.

The analyte monitors and/or analyte monitoring systems (referred to herein collectively as analyte monitoring systems) used with or as systems, devices, and methods for measuring glucose and, optionally, one or more analytes in a bodily fluid may be in vivo analyte monitoring systems or in vitro analyte monitoring systems. In some instances, systems, devices, and methods of the present disclosure may use both in vivo analyte monitoring systems and in vitro analyte monitoring systems.

In vivo analyte monitoring systems include analyte monitoring systems where at least a portion of an analyte sensor is, or can be, positioned in the body of a subject to obtain information about at least one analyte of the body. In vivo analyte monitoring systems can operate without the need for a factory calibration. Examples of in vivo analyte monitoring systems include, but are not limited to, continuous analyte monitoring systems and flash analyte monitoring systems.

Continuous analyte monitoring systems (e.g., continuous glucose monitoring systems), for example, are in vivo systems that can transmit data from a sensor control device to a reader device repeatedly or continuously without prompting (e.g., automatically according to a schedule).

Flash analyte monitoring systems (or flash glucose monitoring systems or simply flash systems), for example, are in vivo systems that can transfer data from a sensor control device in response to a scan or request for data by a reader device, such as with a near field communication (NFC) or radio frequency identification (RFID) protocol.

In vivo analyte monitoring systems can include a sensor that, while positioned in vivo, makes contact with the bodily fluid of the subject and senses one or more analyte levels contained therein. The sensor can be part of a sensor control device that resides on the body of the subject and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few. As used herein, these terms are not limited to devices with analyte sensors, and encompass devices that have sensors of other types, whether biometric or non-biometric. The term "on body" refers to any device that resides directly on the body or in close proximity to the body, such as a wearable device (e.g., glasses, watch, wristband or bracelet, neckband or necklace, etc.).

In vivo analyte monitoring systems can also include one or more reader devices that receive sensed analyte data from the sensor control device. These reader devices can process and/or display the sensed analyte data, in any number of forms, to the subject. These devices, and variations thereof, can be referred to as "handheld reader devices," "reader devices" (or simply, "readers"), "handheld electronics" (or handhelds), "portable data processing" devices or units, "data receivers," "receiver" devices or units (or simply receivers), "relay" devices or units, or "remote" devices or units, to name a few. Other devices such as personal computers have also been utilized with or incorporated into in vivo and in vitro monitoring systems.

For example, referring to FIG. 3, a sensor or portion thereof of an in vivo analyte monitoring system may be the glucose monitor 324, and the reader device may be the health monitoring device 320. In alternative embodiments, the in vivo analyte monitoring system may be, in whole, the glucose monitor 324 that transmits data to a health monitoring device 320, data network 322, data processing terminal/PC3, and/or server/cloud 328.

For in vivo analyte monitoring systems, the determination of one or more physiological parameters (e.g., $k_{gly}$, $k_{age}$ (or $k_{gen}$), and/or K) and/or other analyses described herein may be performed within the in vivo analyte monitoring system, in some instances. Only the physiological parameters may, for example, be determined within the in vivo analyte monitoring system and transmitted to a suitable other component of a physiological parameter analysis system, which may perform other analyses described herein. In some embodiments, the in vivo analyte monitoring system may only produce output signals that correspond to glucose levels that are received by another component of a physiological parameter analysis system. In such cases, one or more of the other component(s) of the physiological parameter analysis system may determine one or more physiological parameters (e.g., $k_{gly}$, $k_{age}$ (or $k_{gen}$), and/or K) and, optionally, perform one or more of the other analyses described herein.

Figure 7:
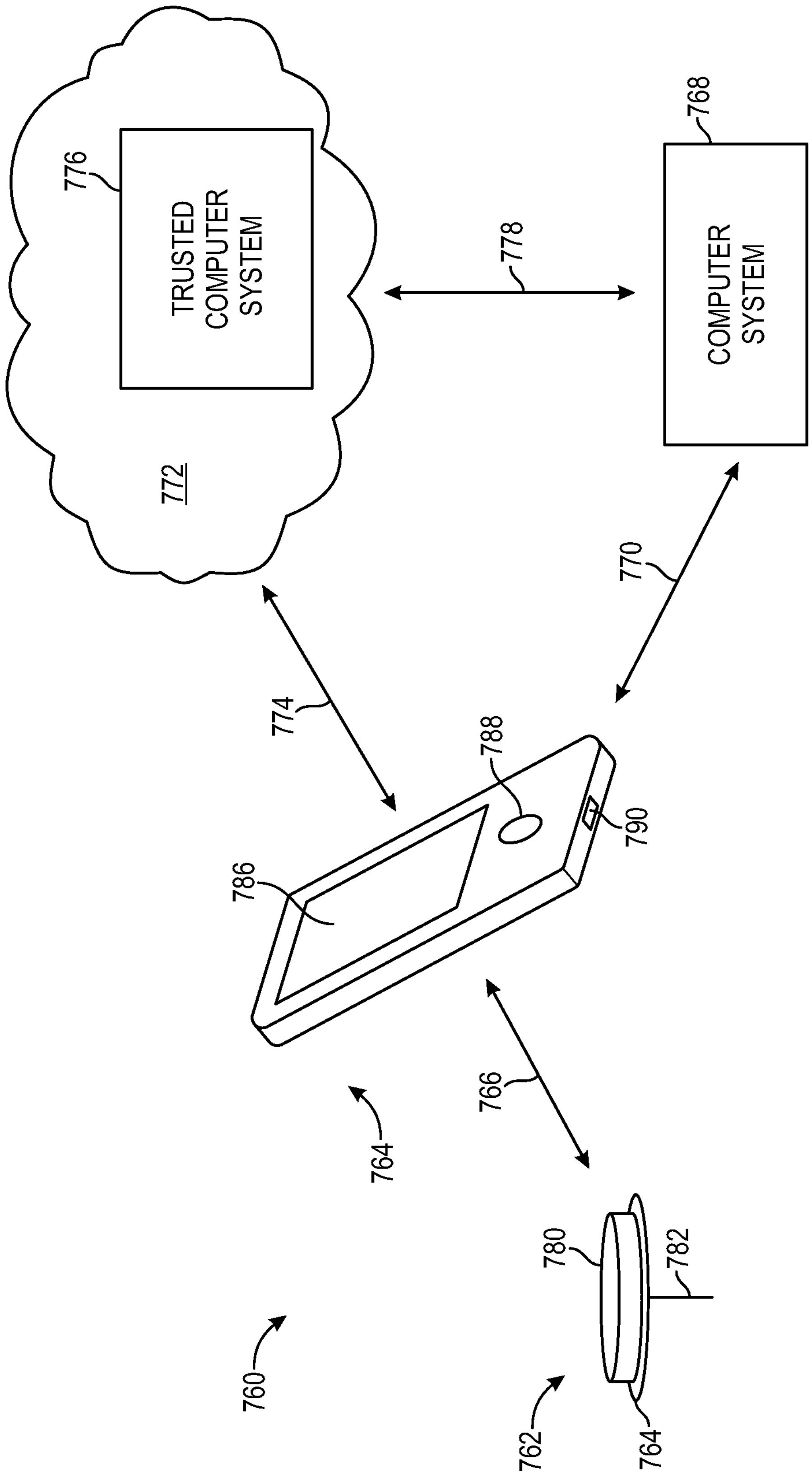
FIG. 7 illustrates an example of an in vivo analyte monitoring system in accordance with some of the embodiments of the present disclosure.

FIG. 7 illustrates an example of an in vivo analyte monitoring system 760. For embodiments of the present disclosure this example in vivo analyte monitoring system 760 monitors glucose and, optionally, one or more other analytes.

The in vivo analyte monitoring system 760 comprises a sensor control device 762 (which may be at least a portion of the glucose monitor 324 of FIG. 3) and a reader device 764 (which may be at least a portion of the health monitoring device 320 of FIG. 3) that communicate with each other over a local communication path (or link) 766, which can be wired or wireless, and uni-directional or bi-directional. In embodiments where path 766 is wireless, a near field communication (NFC) protocol, RFID protocol, BLUETOOTH® or BLUETOOTH® Low Energy protocol, WiFi protocol, proprietary protocol, or the like can be used, including those communication protocols in existence as of the date of this filing or their later developed variants.

Reader device 764 (e.g., a dedicated reader, a cellular phone or PDA running an app, or the like) is also capable of wired, wireless, or combined communication with a computer system 768 (which may be at least a portion of the data processing terminal/PC 326 of FIG. 3) over communication path (or link) 770 and with a network 772 (which may be at least a portion of the data network 322 and/or the server/cloud 328 of FIG. 3), such as the internet or the cloud, over communication path (or link) 774. Communication with network 772 can involve communication with trusted computer system 776 within network 772, or though network 772 to computer system 768 via communication link (or path) 778. Communication paths 770, 774, and 778 can be wireless, wired, or both, can be uni-directional or bi-directional, and can be part of a telecommunications network, such as a Wi-Fi network, a local area network (LAN), a wide area network (WAN), the internet, or other data network. In some cases, communication paths 770 and 774 can be the same path. All communications over paths 766, 770, and 774 can be encrypted and sensor control device 762, reader device 764, computer system 768, and trusted computer system 776 can each be configured to encrypt and decrypt those communications sent and received.

Variants of devices 762 and 764, as well as other components of an in vivo-based analyte monitoring system that are suitable for use with the system, device, and method embodiments set forth herein, are described in US Patent Application Publication No. 2011/0213225 (the '225 Publication), which is incorporated by reference herein in its entirety for all purposes.

Sensor control device 762 can include a housing 780 containing in vivo analyte monitoring circuitry and a power source. In this embodiment, the in vivo analyte monitoring circuitry is electrically coupled with an analyte sensor 782 that extends through an adhesive patch 784 and projects away from housing 780. Adhesive patch 784 contains an adhesive layer (not shown) for attachment to a skin surface of the body of the subject. Other forms of body attachment to the body may be used, in addition to or instead of adhesive.

Sensor 782 is adapted to be at least partially inserted into the body of the subject, where it can make fluid contact with that subject's bodily fluid (e.g., subcutaneous (subdermal) fluid, dermal fluid, or blood) and be used, along with the in vivo analyte monitoring circuitry, to measure analyte-related data of the subject. Sensor 782 and any accompanying sensor control electronics can be applied to the body in any desired manner. For example, an insertion device (not shown) can be used to position all or a portion of analyte sensor 782 through an external surface of the subject's skin and into contact with the subject's bodily fluid. In doing so, the insertion device can also position sensor control device 762 with adhesive patch 784 onto the skin. In other embodiments, insertion device can position sensor 782 first, and then accompanying sensor control electronics can be coupled with sensor 782 afterwards, either manually or with the aid of a mechanical device. Examples of insertion devices are described in US Patent Application Publication Nos. 2008/0009692, 2011/0319729, 2015/0018639, 2015/0025345, and 2015/0173661, all which are incorporated by reference herein in their entireties and for all purposes.

After collecting raw data from the subject's body, sensor control device 762 can apply analog signal conditioning to the data and convert the data into a digital form of the conditioned raw data. In some embodiments, this conditioned raw digital data can be encoded for transmission to another device (e.g., reader device 764), which then algorithmically processes that digital raw data into a final form representative of the subject's measured biometric (e.g., a form readily made suitable for display to the subject or readily used in the analysis module 320B of FIG. 3). This algorithmically processed data can then be formatted or graphically processed for digital display to the subject. In other embodiments, sensor control device 762 can algorithmically process the digital raw data into the final form that is representative of the subject's measured biometric (e.g., analyte level) and then encode and wirelessly communicate that data to reader device 764, which in turn can format or graphically process the received data for digital display to the subject. In other embodiments, sensor control device 762 can graphically process the final form of the data such that it is ready for display, and display that data on a display of sensor control device 762 or transmit the data to reader device 764. In some embodiments, the final form of the biometric data (prior to graphic processing) is used by the system (e.g., incorporated into a diabetes monitoring regime) without processing for display to the subject. In some embodiments, sensor control device 762 and reader device 764 transmit the digital raw data to another computer system for algorithmic processing and display.

Reader device 764 can include a display 786 to output information to the subject (e.g., one or more physiological parameter or an output derived therefrom like cHbA1c) and/or to accept an input from the subject, and an optional input component 788 (or more), such as a button, actuator, touch sensitive switch, capacitive switch, pressure sensitive switch, jog wheel or the like, to input data, commands, or otherwise control the operation of reader device 764. In certain embodiments, display 786 and input component 788 may be integrated into a single component, for example, where the display can measure the presence and location of a physical contact touch upon the display, such as a touch screen subject interface (which may be at least a portion of the subject interface 320A of FIG. 3). In certain embodiments, input component 788 of reader device 764 may include a microphone and reader device 764 may include software configured to analyze audio input received from the microphone, such that functions and operation of the reader device 764 may be controlled by voice commands. In certain embodiments, an output component of reader device 764 includes a speaker (not shown) for outputting information as audible signals. Similar voice responsive components such as a speaker, microphone and software routines to generate, process, and store voice driven signals may be included in sensor control device 762.

Reader device 764 can also include one or more data communication ports 790 for wired data communication with external devices such as computer system 768. Example data communication ports 790 include, but are not limited to, USB ports, mini USB ports, USB Type-C ports, USB micro-A and/or micro-B ports, RS-232 ports, Ethernet ports, Firewire ports, or other similar data communication ports configured to connect to the compatible data cables. Reader device 764 may also include an integrated or attachable in vitro glucose meter, including an in vitro test strip port (not shown) to receive an in vitro glucose test strip for performing in vitro blood glucose measurements.

Reader device 764 can display the measured biometric data wirelessly received from sensor control device 762 and can also be configured to output alarms (e.g., a visual alarm on a display, an auditory alarm, or a combination thereof), alert notifications, glucose levels, etc., which may be visual, audible, tactile, or any combination thereof. Further details and other display embodiments can be found in US Patent Application Publication No. 2011/0193704, for example, which is incorporated herein by reference in its entirety for all purposes.

Reader device 764 can function as a data conduit to transfer the measured data from sensor control device 762 to computer system 768 or trusted computer system 776. In certain embodiments, the data received from sensor control device 762 may be stored (permanently or temporarily) in one or more memories of reader device 764 prior to uploading to computer system 768, trusted computer system 776, or network 772.

Computer system 768 may be a personal computer, a server terminal, a laptop computer, a tablet, or other suitable data processing device. Computer system 768 can be (or include) software for data management and analysis and communication with the components in analyte monitoring system 760. Computer system 768 can be used by the subject, a medical professional, or other user to display and/or analyze the biometric data measured by sensor control device 762. In some embodiments, sensor control device 762 can communicate the biometric data directly to computer system 768 without an intermediary such as reader device 764, or indirectly using an internet connection (also optionally without first sending to reader device 764). Operation and use of computer system 776 is further described in the '225 Publication incorporated herein. Analyte monitoring system 760 can also be configured to operate with a data processing module (not shown), also as described in the incorporated '225 Publication.

Trusted computer system 776 can be within the possession of the manufacturer or distributor of sensor control device 762, either physically or virtually through a secured connection, and can be used to perform authentication of sensor control device 762, for secure storage of the subject's biometric data, and/or as a server that serves a data analytics program (e.g., accessible via a web browser) for performing analysis on the subject's measured data.

In vivo analyte monitoring systems can be used in conjunction with or as a portion of an integrated diabetes management system. For example, an integrated diabetes management system may include an in vivo analyte monitoring system and a supplement/medication delivery system, and more specifically, an in vivo glucose monitoring system and an insulin delivery system (e.g., an insulin pump). Integrated diabetes management systems may be closed-loop, open-loop, or a hybrid thereof. Closed-loop systems are in full control of analyte measurement times and supplement/medication dosages and times. Open-loop systems allow a subject to be in full control of analyte measurement times and supplement/medication dosages and times. Hybrid systems can rely primarily on a closed-loop system methodology but allows a subject to intervene.

In vitro analyte monitoring systems contact a bodily fluid outside of the body. In some instances, in vitro analyte monitoring systems include a meter device that has a port for receiving the bodily fluid of the subject (e.g., on an analyte test strip/swab or via collection of the bodily fluid), which can be analyzed to determine the subject's analyte level.

EXAMPLE EMBODIMENTS

A first nonlimiting example embodiment of the present disclosure is a method comprising: measuring a glucose level of a patient over time; measuring a HbA1c of individual red blood cells in a sample comprising a plurality of red blood cells; deriving a measured cellular HbA1c distribution of the sample; and calculating at least one physiological parameter selected from the group consisting of (a) a red blood cell elimination constant ($k_{age}$), (b) a red blood cell hemoglobin glycation rate constant ($k_{gly}$), and/or (c) an apparent glycation constant (K) based on the measured cellular HbA1c distribution and the glucose levels of the patient over time. The method may further include: using (a), (b), and/or (c) for one or more of the following:

(i) deriving a calculated HbA1c;
(ii) deriving a corrected HbA1c;
(iii) deriving a personalized-target glucose range, a personalized-target glucose upper limit, and/or a personalized-target glucose lower limit;
(iv) deriving a personalized-target average glucose;
(v) deriving a personalized treatment for subject triage;
(vi) deriving a personalized treatment for titration of diabetes medication;
(vii) deriving a personalized closed-loop or hybrid-closed loop control system;
(viii) deriving a personalized treatment using glycation medications;
(ix) identifying abnormal or diseased physiological conditions;
(x) identifying supplements and/or medicines present during testing;
(xi) identifying a physiological age; and
(xii) treating the patient and/or adjusting a treatment of a patient based on one or more values and/or ranges derived and/or identified in (i)-(xii).

A second nonlimiting example embodiment of the present disclosure is a system comprising: an analyte sensor configured to measure a glucose level in a bodily fluid; and a monitoring device comprising: one or more processors; and a memory operatively coupled to the one or more processors storing instructions which, when executed by the one or more processors, causes the one or more processors to: receive a plurality of glucose levels in the bodily fluid over time from the analyte sensor; receive a measured cellular HbA1c distribution; and determine at least one physiological parameter selected from the group consisting of: (a) a red blood cell elimination constant ($k_{age}$), (b) a red blood cell hemoglobin glycation rate constant ($k_{gly}$), and/or (c) an apparent glycation constant (K) based on the measured cellular HbA1c distribution and the glucose levels over time. The instructions which, when executed by the one or more processors, causes the one or more processors to further perform one or more of the following based on (a), (b), and/or (c):

(i) derive a calculated HbA1c;
(ii) derive a corrected HbA1c;
(iii) derive a personalized-target glucose range, a personalized-target glucose upper limit, and/or a personalized-target glucose lower limit;
(iv) derive a personalized-target average glucose;
(v) derive a personalized treatment for subject triage;
(vi) derive a personalized treatment for titration of diabetes medication;
(vii) derive a personalized closed-loop or hybrid-closed loop control system;
(viii) derive a personalized treatment using glycation medications;
(ix) identify abnormal or diseased physiological conditions;
(x) identify supplements and/or medicines present during testing;
(xi) identify a physiological age; and
(xii) treat the patient and/or adjust a treatment of a patient based on one or more values and/or ranges derived and/or identified in (i)-(xii).

Another nonlimiting example embodiment of the present disclosure is a method comprising: measuring a glucose level of a patient over time; measuring a HbA1c of individual red blood cells in a sample comprising a plurality of red blood cells; deriving a measured cellular HbA1c distribution of the sample; and calculating at least one physiological parameter selected from the group consisting of (a) a red blood cell elimination constant ($k_{age}$), (b) a red blood cell glycation rate constant ($k_{gly}$), and/or (c) an apparent glycation constant (K) based on the measured cellular HbA1c distribution and the glucose levels of the patient over time; and adjusting a glucose level target based on the at least one physiological parameter. Said nonlimiting example embodiment may further include one or more of: Element 1: wherein the glucose level target is one or more value selected from the group consisting of a personalized lower glucose limit, a personalized upper glucose limit, and a personalized-target glucose average; Element 2: Element 1 wherein the personalized upper glucose limit is per Equation 23; Element 3: Element 1 and wherein the personalized lower glucose limit is per Equation 21; Element 4: Element 1 and wherein the at least one physiological parameter comprises K, and wherein the personalized-target average glucose (GT) equals AT/(K(1−AT) where AT is a target HbA1c value; Element 5: the method further comprising: treating a subject based on the glucose level target; Element 6: Element 5 and wherein treating the subject comprises administering and/or adjusting: an insulin dosage, a glycation medication dosage, an exercise regime, a meal intake, or a combination thereof; Element 7: wherein the plurality of first glucose levels are measured in a bodily fluid selected from the group consisting of: blood, dermal fluid, interstitial fluid, or a combination thereof; Element 8: the method further comprising: displaying the glucose level target; Element 9: the method further comprising: receiving a glucose level of a subject after adjusting the glucose level target; and displaying an alarm when the glucose level is outside the glucose level target; Element 10: the method further comprising: calculating a metabolic age based on $k_{age}$ and/or K; Element 11: the method further comprising: determining a calculated glycated hemoglobin (cHbA1c) level; and Element 12: the method further comprising: identifying a presence of an abnormal or diseased physiological condition and/or an indicator of doping based on a comparison of the at least one first physiological parameter and the at least one second physiological parameter.

A third nonlimiting example embodiment of the present disclosure is a system for determining a glucose level target comprising: an analyte sensor configured to measure a glucose level in a bodily fluid; and a monitoring device comprising: one or more processors; and a memory operatively coupled to the one or more processors storing instructions which, when executed by the one or more processors, causes the one or more processors to: receive a plurality of glucose levels in the bodily fluid over time from the analyte sensor; receive a measured cellular HbA1c distribution; determine at least one physiological parameter selected from the group consisting of: (a) a red blood cell elimination constant ($k_{age}$), (b) a red blood cell glycation rate constant ($k_{gly}$), and/or (c) an apparent glycation constant (K) based on the measured cellular HbA1c distribution and the glucose levels over time; and adjust a glucose level target based on the at least one physiological parameter. Said nonlimiting example embodiment may further include one or more of: Element 13: wherein the glucose level target is one or more value selected from the group consisting of a personalized lower glucose limit, a personalized upper glucose limit, and a personalized-target glucose average; Element 14: wherein the at least one physiological parameter comprises $k_{gly}$, and wherein the personalized upper glucose limit can be calculated with Equation 23; Element 15: wherein the at least one physiological parameter comprises $k_{gly}$, and wherein the personalized lower glucose limit can be calculated with equation 21.; Element 16: wherein the at least one physiological parameter comprises K, and wherein the personalized-target average glucose (GT) per Equation 26 or 27 or 28; Element 17: the system further comprising: a display, wherein the instructions which, when executed by the one or more processors, causes the one or more processors to further: display the glucose level target; Element 18: wherein the instructions which, when executed by the one or more processors, causes the one or more processors to further: determine a metabolic age based on $k_{age}$ and/or K; Element 19: wherein the instructions which, when executed by the one or more processors, causes the one or more processors to further: determine a calculated glycated hemoglobin (cHbA1c); Element 20: wherein the instructions which, when executed by the one or more processors, causes the one or more processors to further: identify a presence of an abnormal or diseased physiological condition and/or an indicator of doping based on a comparison of the at least one first physiological parameter and the at least one second physiological parameter; and Element 21: wherein the instructions, when executed, cause the one or more processors to: determine an insulin dosage based on the glucose level target; and transmit the insulin dosage to an insulin pump system.

A fourth nonlimiting example embodiment of the present disclosure is a method comprising: receiving (and/or measuring) a plurality of first glucose levels for a subject over time; receiving (and/or measuring) a HbA1c level of individual red blood cells in a sample comprising a plurality of red blood cells; deriving a measured cellular HbA1c distribution of the sample based on the HbA1c level of individual red blood cells; and calculating at least one physiological parameter selected from the group consisting of (a) a red blood cell elimination constant ($k_{age}$), (b) a red blood cell glycation rate constant ($k_{gly}$), and/or (c) an apparent glycation constant (K) based on the measured cellular HbA1c distribution and the glucose levels of the subject over time. Measuring glucose levels may involve sampling a bodily fluid from the subject using an analyte sensor; and measuring the plurality of first glucose levels with the analyte sensor. The fourth nonlimiting example embodiment may further include one or more of: Element 25: the method further comprising: receiving (and/or measuring) a plurality of second glucose levels for the subject over a time period; and deriving a calculated HbA1c (cHbA1c) level (e.g., using Equation 17 or 18) for the subject based on the at least one physiological parameter and the plurality of second glucose levels; Element 26: Element 25 and the method further comprising: diagnosing, treating, and/or monitoring the subject based on the cHbA1c level; Element 27: Element 26 and wherein treating the subject occurs and comprises administering and/or adjusting: an insulin dosage, a glycation medication dosage, an exercise regime, a meal intake, or a combination thereof; Element 28: Element 25 and the method further comprising: displaying the cHbA1c level (e.g., on a system 210, a system 310, a glucose measurement device and/or closed-loop insulin pump system from which the plurality of first and/or second glucose levels were measured, or the like); Element 29: Element 25 and the method further comprising: calculating an adjusted HbA1c (aHbA1c) level for the subject based on the cHbA1c level, the $k_{age}$, and a defined reference $k_{age}$ ($k^{ref}_{age}$) (e.g., using Equation 19); Element 30: the method further comprising: receiving (and/or measuring) a laboratory measured HbA1c level for the subject; and calculating an adjusted HbA1c (aHbA1c) level for the subject based on the laboratory measured HbA1c level, the $k_{age}$, and a defined reference $k_{age}$ ($k^{ref}_{age}$) (e.g., using Equation 19); Element 31: Element 25 and the method further comprising: calculating an adjusted HbA1c (aHbA1c) level for the subject based on the cHbA1c level, the K, and a defined reference K ($K^{ref}$) (e.g., using Equation 20); Element 32: the method further comprising: receiving (and/or measuring) a laboratory measured HbA1c level for the subject; and calculating an adjusted HbA1c (aHbA1c) level for the subject based on the laboratory measured HbA1c level, the K, and a defined reference K ($K^{ref}$) (e.g., using Equation 20); Element 33: Element 29 or Element 30 or Element 31 or Element 32 and the method further comprising: diagnosing, treating, and/or monitoring the subject based on the aHbA1c level; Element 34: Element 33 and wherein treating the subject occurs and comprises administering and/or adjusting: an insulin dosage, a glycation medication dosage, an exercise regime, a meal intake, or a combination thereof; Element 35: Element 29 or Element 30 or Element 31 or Element 32 and the method further comprising: displaying the cHbA1c level and/or the aHbA1c level (e.g., on a system 210, a system 310, a glucose measurement device and/or closed-loop insulin pump system from which the plurality of first and/or second glucose levels were measured, or the like); Element 36: Element 29 or Element 30 or Element 31 or Element 32 and the method further comprising: deriving a personalized-target glucose range (e.g., using Equations 22 and 24), a personalized glucose upper limit (e.g., using Equation 24), and/or a personalized glucose lower limit (e.g., using Equation 22, based on the aHbA1c level and a laboratory measured HbA1c; Element 37: Element 36 and the method further comprising: diagnosing, treating, and/or monitoring the subject based on the personalized-target glucose range, the personalized glucose upper limit, and/or the personalized glucose lower limit; Element 38: Element 37 and wherein treating the subject occurs and comprises administering and/or adjusting: an insulin dosage, a glycation medication dosage, an exercise regime, a meal intake, or a combination thereof; Element 39: Element 36 and the method further comprising: displaying the personalized-target glucose range, the personalized glucose upper limit, and/or the personalized glucose lower limit (e.g., on a system 210, a system 310, a glucose measurement device and/or closed-loop insulin pump system from which the plurality of first and/or second glucose levels were measured, or the like); Element 40: Element 36 and the method further comprising: receiving a glucose level for the subject after deriving the personalized-target glucose range, the personalized glucose upper limit, and/or the personalized glucose lower limit; and displaying (visually, audibly, and/or haptically (relating to touch)) an alarm when the glucose level is outside the personalized-target glucose range, above the personalized glucose upper limit, and/or below the personalized glucose lower limit; Element 41: Element 29 or Element 30 or Element 31 or Element 32 and the method further comprising: deriving a personalized-target average glucose (e.g., using Equation 26 or 27 or 28); Element 42: Element 41 and the method further comprising: diagnosing, treating, and/or monitoring the subject based on the personalized-target average glucose; Element 43: Element 42 and wherein treating the subject occurs and comprises administering and/or adjusting: an insulin dosage, a glycation medication dosage, an exercise regime, a meal intake, or a combination thereof; Element 44: Element 41 and the method further comprising: displaying the personalized-target average glucose (e.g., on a system 210, a system 310, a glucose measurement device and/or closed-loop insulin pump system from which the plurality of first and/or second glucose levels were measured, or the like); Element 45: Element 29 or Element 30 or Element 31 or Element 32 and the method further comprising one or more of the following based, at least in part, on the aHbA1c level: deriving a personalized treatment for subject triage; deriving a personalized treatment for titration of diabetes medication; deriving a personalized closed-loop or hybrid-closed loop control system; deriving a personalized treatment using glycation medications; identifying abnormal or diseased physiological conditions; identifying supplements and/or medicines present during testing; and identifying a physiological age; Element 46: Element 25 and the method further comprising one or more of the following based, at least in part, on the cHbA1c level: deriving a personalized treatment for subject triage; deriving a personalized treatment for titration of diabetes medication; deriving a personalized closed-loop or hybrid-closed loop control system; deriving a personalized treatment using glycation medications; identifying abnormal or diseased physiological conditions; identifying supplements and/or medicines present during testing; and identifying a physiological age; Element 47: the method further comprising: deriving a personalized-target glucose range (e.g., using Equations 21 and 23), a personalized glucose upper limit (e.g., using Equation 23), and/or a personalized glucose lower limit (e.g., using Equation 21) based on the $k_{gly}$ and a defined reference $k_{gly}$ ($k^{ref}_{gly}$); Element 48: Element 47 and the method further comprising: diagnosing, treating, and/or monitoring the subject based on the personalized-target glucose range, the personalized glucose upper limit, and/or the personalized glucose lower limit; Element 49: Element 48 and wherein treating the subject occurs and comprises administering and/or adjusting: an insulin dosage, a glycation medication dosage, an exercise regime, a meal intake, or a combination thereof; Element 50: Element 47 and the method further comprising: displaying the personalized-target glucose range, the personalized glucose upper limit, and/or the personalized glucose lower limit (e.g., on a system 210, a system 310, a glucose measurement device and/or closed-loop insulin pump system from which the plurality of first and/or second glucose levels were measured, or the like); Element 51: Element 47 and the method further comprising: receiving a glucose level for the subject after deriving the personalized-target glucose range, the personalized glucose upper limit, and/or the personalized glucose lower limit; and displaying (visually, audibly, and/or haptically (relating to touch)) an alarm when the glucose level is outside the personalized-target glucose range, above the personalized glucose upper limit, and/or below the personalized glucose lower limit; Element 52: the method further comprising: deriving a personalized glucose level (e.g., using Equation 25 or Equation 26) based on the $k_{gly}$, a defined reference $k_{gly}$ ($k^{ref}_{gly}$), and a measured glucose level; Element 53: Element 52 and the method further comprising: diagnosing, treating, and/or monitoring the subject based on the personalized glucose level (e.g., the personalized glucose level relative to a currently accepted glucose range or an intracellular glucose level relative to a currently accepted intracellular glucose level range (i.e., LIGL-UIGL)); Element 54: Element 53 and wherein treating the subject occurs and comprises administering and/or adjusting: an insulin dosage, a glycation medication dosage, an exercise regime, a meal intake, or a combination thereof; Element 55: Element 52 and the method further comprising: displaying the personalized glucose level (e.g., on a system 310, a system 410, a glucose measurement device and/or closed-loop insulin pump system from which the plurality of first and/or second glucose levels were measured, or the like); and Element 56: Element 52 and the method further comprising: displaying (visually, audibly, and/or haptically (relating to touch)) an alarm when the personalized glucose level is outside currently accepted respective glucose range.

A fifth nonlimiting example embodiment of the present disclosure is an analyte sensor configured to measure a glucose level in a bodily fluid; and a monitoring device comprising: one or more processors; and a memory operatively coupled to the one or more processors storing instructions which, when executed by the one or more processors, causes the analyte sensor (or a larger system the analyte sensor is a portion of) to perform the method of fourth nonlimiting example embodiment optionally including one or more of Elements 25-56.

A sixth nonlimiting example embodiment of the present disclosure is closed-loop insulin pump systems comprising: an analyte sensor configured to measure a glucose level in a bodily fluid; an insulin pump; and a monitoring device comprising: one or more processors; and a memory operatively coupled to the one or more processors storing instructions which, when executed by the one or more processors, causes the system to perform the method of fourth nonlimiting example embodiment (optionally including one or more of Elements 25-56), where, when treatment is administered, said treatment includes administering via the closed-loop insulin pump systems an insulin dosage.

A seventh nonlimiting example embodiment is a method comprising: determining at least one physiological parameter for a subject selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) a plurality of first glucose levels and (2) a HbA1c level of individual red blood cells in a sample comprising a plurality of red blood cells using a model that considers cross-membrane glucose transport and glycation; receiving (and/or measuring) a plurality of second glucose levels for the subject over a time period; and deriving a calculated HbA1c (cHbA1c) level (e.g., using Equation 17 or 18) for the subject based on the at least one physiological parameter and the plurality of second glucose levels. Further embodiments may further include one or more of Elements 26-46.

A eighth nonlimiting example embodiment is a method comprising: receiving (and/or measuring) a plurality of first glucose levels for a subject over a first time period; receiving (and/or measuring) a first glycated hemoglobin (HbA1c) level for the subject corresponding to an end of the first time period; determining at least one physiological parameter for the subject selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of first glucose levels and (2) the first HbA1c level using a model that considers cross-membrane glucose transport and glycation; receiving (and/or measuring) a plurality of second glucose levels for the subject over a second time period; and deriving a calculated HbA1c (cHbA1c) level (e.g., using Equation 17 or 18) based on the at least one physiological parameter and the plurality of second glucose levels. Further embodiments may further include one or more of Elements 26-46.

A ninth nonlimiting example embodiment of the present disclosure is an analyte sensor configured to measure a glucose level in a bodily fluid; and a monitoring device comprising: one or more processors; and a memory operatively coupled to the one or more processors storing instructions which, when executed by the one or more processors, causes the analyte sensor (or a larger system that the analyte sensor is part of) to perform the method of seventh or eighth nonlimiting example embodiment (optionally including include one or more of Elements 26-46).

A tenth nonlimiting example embodiment of the present disclosure is a closed-loop insulin pump systems comprising: an analyte sensor configured to measure a glucose level in a bodily fluid; an insulin pump; and a monitoring device comprising: one or more processors; and a memory operatively coupled to the one or more processors storing instructions which, when executed by the one or more processors, causes the system to perform the method of seventh or eighth nonlimiting example embodiment (optionally including include one or more of Elements 26-46), where, when treatment is administered, said treatment includes administering via the closed-loop insulin pump systems an insulin dosage.

A eleventh nonlimiting example embodiment of the present disclosure is a method comprising: receiving (and/or measuring) a laboratory measured HbA1c for a subject; determining a red blood cell turnover rate ($k_{age}$) for the subject based on (1) a plurality of first glucose levels and (2) a HbA1c level of individual red blood cells in a sample comprising a plurality of red blood cells using a model that considers cross-membrane glucose transport and glycation; and calculating an adjusted HbA1c (aHbA1c) level for the subject based on the HbA1c level, the $k_{age}$, and a defined reference $k_{age}$ ($k^{ref}_{age}$) (e.g., using Equation 19)

A twelfth nonlimiting example embodiment of the present disclosure is a method comprising: receiving (and/or measuring) a laboratory measured HbA1c level for a subject; determining a red blood cell turnover rate ($k_{age}$) for the subject based on (1) a plurality of first glucose levels and (2) a HbA1c level of individual red blood cells in a sample comprising a plurality of red blood cells using a model that considers cross-membrane glucose transport and glycation; and calculating an adjusted HbA1c (aHbA1c) level for the subject based on the HbA1c level, the K, and a defined reference K ($K^{ref}$) (e.g., using (Equation 20).

A thirteenth nonlimiting example embodiment of the present disclosure is an analyte sensor configured to measure a glucose level in a bodily fluid; and a monitoring device comprising: one or more processors; and a memory operatively coupled to the one or more processors storing instructions which, when executed by the one or more processors, causes the analyte sensor (or a larger system that the analyte sensor is part of) to perform the method of eleventh or twelfth nonlimiting example embodiment (optionally including include one or more of Elements 33-45).

A fourteenth nonlimiting example embodiment of the present disclosure is a closed-loop insulin pump systems comprising: an analyte sensor configured to measure a glucose level in a bodily fluid; an insulin pump; and a monitoring device comprising: one or more processors; and a memory operatively coupled to the one or more processors storing instructions which, when executed by the one or more processors, causes the system to perform the method of eleventh or twelfth nonlimiting example embodiment (optionally including include one or more of Elements 33-45), where, when treatment is administered, said treatment includes administering via the closed-loop insulin pump systems an insulin dosage.

An fifteenth nonlimiting example embodiment of the present disclosure is a method comprising: receiving (and/or measuring) a plurality of first glucose levels for a subject over time; receiving (and/or measuring) a HbA1c level of individual red blood cells in a sample comprising a plurality of red blood cells; deriving a measured cellular HbA1c distribution of the sample based on the HbA1c level of individual red blood cells; and calculating at least one physiological parameter selected from the group consisting of (a) a red blood cell elimination constant ($k_{age}$), (b) a red blood cell glycation rate constant ($k_{gly}$), and/or (c) an apparent glycation constant (K) based on the measured cellular HbA1c distribution and the glucose levels of the subject over time; and deriving a personalized glucose level (e.g., using Equation 25 or Equation 26) based on the $k_{gly}$, a defined reference $k_{gly}$ ($k^{ref}_{gly}$), and the measured glucose level. Measuring glucose levels may involve sampling a bodily fluid from the subject using an analyte sensor; and measuring the plurality of first glucose levels with the analyte sensor. The fifteenth nonlimiting example embodiment may further include one or more of: Element 60: and the method further comprising: diagnosing, treating, and/or monitoring the subject based on the personalized glucose level (e.g., the personalized glucose level relative to a currently accepted glucose range or an intracellular glucose level relative to a currently accepted intracellular glucose level range (i.e., LIGL-UIGL)); Element 61: Element 60 and wherein treating the subject occurs and comprises administering and/or adjusting: an insulin dosage, a glycation medication dosage, an exercise regime, a meal intake, or a combination thereof; Element 62: the method further comprising: displaying the personalized glucose level (e.g., on a system 310, a system 410, a glucose measurement device and/or closed-loop insulin pump system from which the plurality of first and/or second glucose levels were measured, or the like); and Element 63: the method further comprising: displaying (visually, audibly, and/or haptically (relating to touch)) an alarm when the personalized glucose level is outside currently accepted respective glucose range A sixteenth nonlimiting example embodiment of the present disclosure is an analyte sensor configured to measure a glucose level in a bodily fluid; and a monitoring device comprising: one or more processors; and a memory operatively coupled to the one or more processors storing instructions which, when executed by the one or more processors, causes the one or more processors to perform the method of the fifteenth nonlimiting example embodiment optionally including one or more of Elements 60-63.

A fourteenth nonlimiting example embodiment of the present disclosure is closed-loop insulin pump systems comprising: an analyte sensor configured to measure a glucose level in a bodily fluid; an insulin pump; and a monitoring device comprising: one or more processors; and a memory operatively coupled to the one or more processors storing instructions which, when executed by the one or more processors, causes the one or more processors to perform the method of the fifteenth nonlimiting example embodiment (optionally including one or more of Elements 60-63), where, when treatment is administered, said treatment includes administering via the closed-loop insulin pump systems an insulin dosage.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. A method for improving glucose management of a subject by treating the subject using improved physiological parameters comprising:

receiving a plurality of first glucose levels for the subject over time;

receiving an HbA1c level of individual red blood cells in a sample comprising a plurality of red blood cells;

receiving a cellular HbA1c distribution of the sample based on the HbA1c level of individual red blood cells;

calculating, based on the cellular HbA1c distribution and the glucose levels of the subject over time, at least one physiological parameter selected from the group consisting of:

(a) a red blood cell elimination constant ($k_{age}$), (b) a red blood cell glycation rate constant ($k_{gly}$), and/or (c) an apparent glycation constant (K); and treating the subject based on the at least one physiological parameter by administering or adjusting: an insulin dosage, a glycation medication dosage, an exercise regime, a meal intake, or a combination thereof.

2. The method of claim 1, wherein measuring the plurality of first glucose levels comprises:

sampling a bodily fluid from the subject using an analyte sensor; and measuring the plurality of first glucose levels with the analyte sensor.

3. The method of claim 1 further comprising:

deriving a personalized-target glucose range, a personalized glucose upper limit, and/or a personalized glucose lower limit based on the $k_{gly}$ and a defined reference $k_{gly}$ ($k^{ref}_{gly}$); and diagnosing, treating, and/or monitoring the subject based on the personalized-target glucose range, the personalized glucose upper limit, and/or the personalized glucose lower limit.

4. The method of claim 1 further comprising:

deriving a personalized-target glucose range, a personalized glucose upper limit, and/or a personalized glucose lower limit based on the $k_{gly}$ and a defined reference $k_{gly}$ ($k^{ref}_{gly}$);

receiving a received glucose level for the subject; and displaying an alarm when the received glucose level is outside the personalized-target glucose range, above the personalized glucose upper limit, and/or below the personalized glucose lower limit.

5. The method of claim 1 further comprising:

deriving a personalized-target glucose range, a personalized glucose upper limit, and/or a personalized glucose lower limit based on the $k_{gly}$ and a defined reference $k_{gly}$ ($k^{ref}_{gly}$);

receiving a received glucose level for the subject; and displaying the personalized-target glucose range, the personalized glucose upper limit, and/or the personalized glucose lower limit.

6. The method of claim 1 further comprising:

receiving a plurality of second glucose levels for the subject over a time period; and deriving a calculated HbA1c (cHbA1c) level for the subject based on the at least one physiological parameter and the plurality of second glucose levels.

7. The method of claim 6 further comprising:

displaying the cHbA1c level.

8. The method of claim 6 further comprising:

treating the subject based on the cHbA1c level by administering and/or adjusting: an insulin dosage, a glycation medication dosage, an exercise regime, a meal intake, or a combination thereof.

9. The method of claim 6 further comprising:

calculating an adjusted HbA1c (aHbA1c) level for the subject based on the cHbA1c level, the $k_{age}$, and a defined reference $k_{age}$ ($k^{ref}_{age}$).

10. The method of claim 6 further comprising:

calculating an adjusted HbA1c (aHbA1c) level for the subject based on the cHbA1c level, the K, and a defined reference K ($K^{ref}$).

11. The method of claim 1 further comprising:

receiving a laboratory measured HbA1c level for the subject; and calculating an adjusted HbA1c (aHbA1c) level for the subject based on the laboratory measured HbA1c level, the $k_{age}$, and a defined reference $k_{age}$ ($k^{ref}_{age}$).

12. The method of claim 1 further comprising:

receiving a laboratory measured HbA1c level for the subject; and calculating an adjusted HbA1c (aHbA1c) level for the subject based on the laboratory measured HbA1c level, the K, and a defined reference K ($K^{ref}$).

13. A system for improving glucose management of a subject by treating the subject using improved physiological parameters comprising:

an analyte sensor configured to measure a glucose level in a bodily fluid;

one or more processors; and a memory operatively coupled to the one or more processors storing instructions which, when executed by the one or more processors, causes the system to perform a method comprising:

receiving a plurality of first glucose levels for the subject over time using the analyte sensor;

receiving an HbA1c level of individual red blood cells in a sample comprising a plurality of red blood cells;

receiving a cellular HbA1c distribution of the sample based on the HbA1c level of individual red blood cells;

calculating, based on the cellular HbA1c distribution and the glucose levels of the subject over time, at least one physiological parameter selected from the group consisting of:

(a) a red blood cell elimination constant ($k_{age}$), (b) a red blood cell glycation rate constant ($k_{gly}$), and/or (c) an apparent glycation constant (K); and treating the subject based on the at least one physiological parameter by administering or adjusting: an insulin dosage, a glycation medication dosage, an exercise regime, a meal intake, or a combination thereof.

14. The system of claim 13, wherein the method further comprises:

deriving a personalized-target glucose range, a personalized glucose upper limit, and/or a personalized glucose lower limit based on the $k_{gly}$ and a defined reference $k_{gly}$ ($k^{ref}_{gly}$);

causing the system to measure a measured glucose level for the subject; and displaying an alarm when the measured glucose level is outside the personalized-target glucose range, above the personalized glucose upper limit, and/or below the personalized glucose lower limit.

15. The system of claim 13, wherein the method further comprises:

deriving a personalized-target glucose range, a personalized glucose upper limit, and/or a personalized glucose lower limit based on the $k_{gly}$ and a defined reference $k_{gly}$ ($k^{ref}_{gly}$), receiving a received glucose level for the subject; and displaying on the system the personalized-target glucose range, the personalized glucose upper limit, and/or the personalized glucose lower limit.

16. The system of claim 13, wherein the method further comprises:

receiving a plurality of second glucose levels for the subject over a time period; and deriving a calculated HbA1c (cHbA1c) level for the subject based on the at least one physiological parameter and the plurality of second glucose levels.

17. The system of claim 16, wherein the method further comprises:

displaying on the system the cHbA1c level.

18. The system of claim 16, wherein the method further comprises:

calculating an adjusted HbA1c (aHbA1c) level for the subject based on the cHbA1c level, the $k_{age}$, and a defined reference $k_{age}$ ($k^{ref}_{age}$).

19. The system of claim 16, wherein the method further comprises:

calculating an adjusted HbA1c (aHbA1c) level for the subject based on the cHbA1c level, the K, and a defined reference K ($K^{ref}$).

20. A closed-loop insulin pump system for improving glucose management of a subject by treating the subject using improved physiological parameters comprising:

an analyte sensor configured to measure a glucose level in a bodily fluid;

an insulin pump;

one or more processors; and a memory operatively coupled to the one or more processors storing instructions which, when executed by the one or more processors, causes the system to perform a method comprising:

receiving a plurality of first glucose levels for a subject over time using the analyte sensor;

receiving an HbA1c level of individual red blood cells in a sample comprising a plurality of red blood cells;

receiving a cellular HbA1c distribution of the sample based on the HbA1c level of individual red blood cells; and calculating, based on the measured cellular HbA1c distribution and the glucose levels of the subject over time, at least one physiological parameter selected from the group consisting of:

(a) a red blood cell elimination constant ($k_{age}$), (b) a red blood cell glycation rate constant ($k_{gly}$), and/or (c) an apparent glycation constant (K); and administering via the closed-loop insulin pump system an insulin dosage based on at least one of the physiological parameter.

* * * * *